United States Patent
Yamada et al.

(10) Patent No.: US 10,170,710 B2
(45) Date of Patent: Jan. 1, 2019

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Yui Yamada, Kanagawa (JP); Hideko Inoue, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 57 days.

(21) Appl. No.: 15/156,679

(22) Filed: May 17, 2016

(65) Prior Publication Data
US 2016/0343960 A1    Nov. 24, 2016

(30) Foreign Application Priority Data
May 20, 2015    (JP) .................... 2015-102410

(51) Int. Cl.
*C07F 15/00*    (2006.01)
*H01L 51/00*    (2006.01)
(Continued)

(52) U.S. Cl.
CPC ........ *H01L 51/0087* (2013.01); *C07D 471/04* (2013.01); *C07F 15/0086* (2013.01);
(Continued)

(58) Field of Classification Search
CPC ... C07D 471/04; C07F 15/0086; C09K 11/06; C09K 2211/185; C09K 2211/1007;
(Continued)

(56) References Cited

U.S. PATENT DOCUMENTS 7,041,390 B2    5/2006    Seo et al.
7,176,307 B2    2/2007    Seo et al.
(Continued)

FOREIGN PATENT DOCUMENTS

JP    2009-023938 A    2/2009
WO    WO 2004/081019 A1    9/2004
(Continued)

*Primary Examiner* — Satya B Sastri
(74) *Attorney, Agent, or Firm* — Husch Blackwell LLP

(57) ABSTRACT

Provided is an organometallic complex which emits light with a short wavelength and has high emission efficiency and high heat resistance. The organometallic complex includes a central metal; and a first ligand, a second ligand, a third ligand, and a fourth ligand which are coordinated to the central metal. The first ligand includes a triazole skeleton including nitrogen bonded to the central metal. The second ligand includes an indolo[3,2-b]carbazole skeleton whose 6-position is bonded to the central metal or a pyrido[2,3-b: 6,5-b']diindole skeleton whose 6-position is bonded to the central metal. The third ligand includes a benzene skeleton whose carbon is bonded to the central metal. The fourth ligand includes a pyridine skeleton whose nitrogen is bonded to the central metal or a benzene skeleton whose carbon is bonded to the central metal.

12 Claims, 24 Drawing Sheets

(51) Int. Cl.
*C09K 11/06* (2006.01)
*H01L 27/32* (2006.01)
*H01L 51/52* (2006.01)
*C23C 16/42* (2006.01)
*C07D 471/04* (2006.01)
*H01L 27/12* (2006.01)
*H01L 51/50* (2006.01)

(52) U.S. Cl.
CPC .............. *C09K 11/06* (2013.01); *C23C 16/42* (2013.01); *H01L 27/3262* (2013.01); *C09K 2211/1007* (2013.01); *C09K 2211/1029* (2013.01); *C09K 2211/1059* (2013.01); *C09K 2211/185* (2013.01); *H01L 27/1214* (2013.01); *H01L 51/5016* (2013.01)

(58) Field of Classification Search
CPC .... C09K 2211/1029; C09K 2211/1059; H01L 27/1214; H01L 27/3262; H01L 51/0087; H01L 51/5016
See application file for complete search history.

(56) References Cited

U.S. PATENT DOCUMENTS

| | | | |
|---|---|---|---|
| 8,816,080 | B2 | 8/2014 | Li et al. |
| 8,927,713 | B2 | 1/2015 | Li et al. |
| 8,981,366 | B2 | 3/2015 | Kadoma et al. |
| 9,238,668 | B2 | 1/2016 | Li et al. |
| 2011/0057179 | A1* | 3/2011 | Nowatari ............ H01L 51/5278 257/40 |
| 2013/0168656 | A1 | 7/2013 | Tsai et al. |
| 2014/0034924 | A1 | 2/2014 | Kawata et al. |
| 2015/0105556 | A1* | 4/2015 | Li ......................... C09K 11/06 546/4 |
| 2015/0287938 | A1 | 10/2015 | Li et al. |
| 2016/0322590 | A1 | 11/2016 | Inoue et al. |
| 2017/0062738 | A1 | 3/2017 | Yamaguchi et al. |

FOREIGN PATENT DOCUMENTS

| | | |
|---|---|---|
| WO | WO 2009/011447 A2 | 1/2009 |
| WO | WO 2012/112853 A1 | 8/2012 |
| WO | WO 2012/162488 A1 | 11/2012 |

\* cited by examiner

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic complex, particularly, to an organometallic complex that is capable of converting triplet excitation energy into light emission. In addition, one embodiment of the present invention relates to a light-emitting element, a light-emitting device, an electronic device, and a lighting device each including the organometallic complex. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a power storage device, a memory device, a method of driving any of them, and a method of manufacturing any of them.

2. Description of the Related Art

A light-emitting element having a structure in which an organic compound that is a light-emitting substance is provided between a pair of electrodes (also referred to as an organic EL element) has attracted attention as a next-generation flat panel display in terms of characteristics such as being thin and light in weight, high-speed response, and low voltage driving. When a voltage is applied to this organic EL element (light-emitting element), electrons and holes injected from the electrodes recombine to put the light-emitting substance into an excited state, and then light is emitted in returning from the excited state to the ground state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3.

Among the above light-emitting substances, a compound capable of converting singlet excitation energy into light emission is called a fluorescent compound (fluorescent material), and a compound capable of converting triplet excitation energy into light emission is called a phosphorescent compound (phosphorescent material).

Accordingly, the internal quantum efficiency (the ratio of the number of generated photons to the number of injected carriers) of a light-emitting element including a fluorescent material is thought to have a theoretical limit of 25%, on the basis of S*:T*=1:3, while the internal quantum efficiency of a light-emitting element including a phosphorescent material is thought to have a theoretical limit of 75%.

In other words, a light-emitting element including a phosphorescent material has higher efficiency than a light-emitting element including a fluorescent material. Thus, various kinds of phosphorescent materials have been actively developed in recent years. An organometallic complex that contains iridium or the like as a central metal is particularly attracting attention because of its high phosphorescence quantum yield (for example, see Patent Document 1).

REFERENCE

Patent Document

[Patent Document 1] Japanese Published Patent Application No. 2009-023938

SUMMARY OF THE INVENTION

Although phosphorescent materials exhibiting excellent characteristics have been actively developed as disclosed in Patent Document 1, development of novel materials with better characteristics has been desired.

In view of the above, according to one embodiment of the present invention, a novel organometallic complex is provided. In particular, a novel organometallic complex emitting light with a short wavelength, which is a phosphorescent material that has been especially desired to be developed, is provided. According to one embodiment of the present invention, a novel organometallic complex with a high emission quantum efficiency is provided. According to one embodiment of the present invention, a novel organometallic complex which achieves improved color purity by a reduction of half width of an emission spectrum is provided. Furthermore, a novel organometallic complex with an excellent sublimation property is provided. According to one embodiment of the present invention, a novel organometallic complex that can be used in a light-emitting element is provided. According to one embodiment of the present invention, a novel organometallic complex that can be used in an EL layer of a light-emitting element is provided. According to one embodiment of the present invention, a novel light-emitting element is provided. In addition, according to one embodiment of the present invention, a novel light-emitting device, a novel electronic device, or a novel lighting device is provided. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an organometallic complex including a central metal; and a first ligand, a second ligand, a third ligand, and a fourth ligand which are coordinated to the central metal. The first ligand includes a triazole skeleton including nitrogen bonded to the central metal. The second ligand includes an indolo[3,2-b]carbazole skeleton whose 6-position is bonded to the central metal or a pyrido[2,3-b:6,5-b']diindole skeleton whose 6-position is bonded to the central metal. The third ligand includes a benzene skeleton whose carbon is bonded to the central metal. The fourth ligand includes a pyridine skeleton whose nitrogen is bonded to the central metal or a benzene skeleton whose carbon is bonded to the central metal.

Another embodiment of the present invention is an organometallic complex represented by a general formula (G1) below.

(G1)

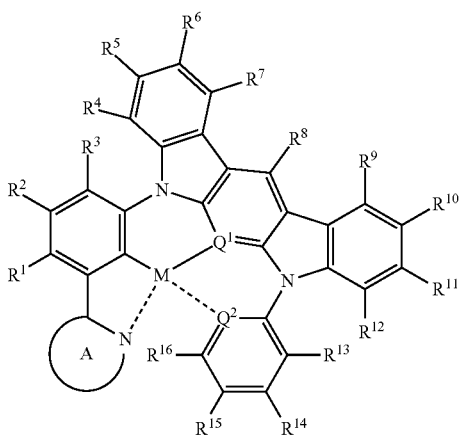

In the general formula (G1), M represents Pt or Pd. Each of $R^1$ to $R^{16}$ independently represents any of hydrogen, an alkyl group having 1 to 6 carbon atoms, and a substituted or unsubstituted aryl group having 6 to 13 carbon atoms. One of $Q^1$ and $Q^2$ represents nitrogen, and the other thereof represents carbon. Furthermore, a ring A represents a triazole ring.

Another embodiment of the present invention is an organometallic complex represented by a general formula (G1-1) or a general formula (G1-2) below.

(G1-1)

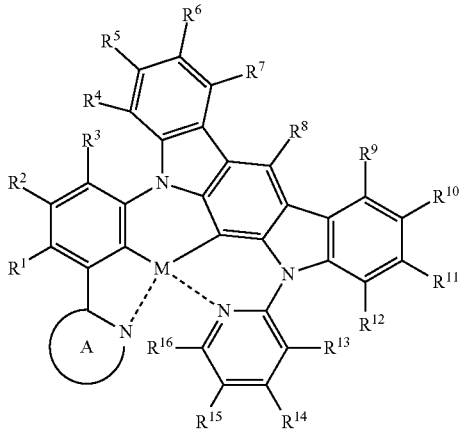

(G1-2)

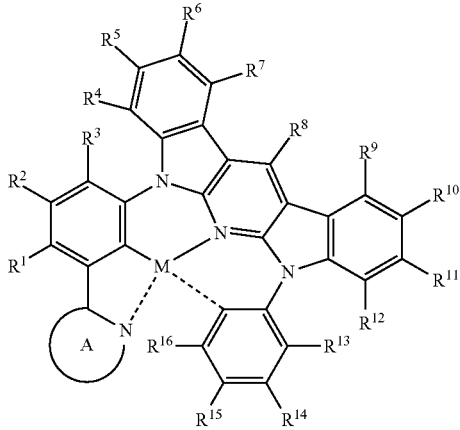

Note that in the general formula (G1-1) or the general formula (G1-2), M represents Pt or Pd. Each of $R^1$ to $R^{16}$ independently represents any of hydrogen, an alkyl group having 1 to 6 carbon atoms, and a substituted or unsubstituted aryl group having 6 to 13 carbon atoms. Furthermore, a ring A represents a triazole ring.

When the ring A is represented by the general formula (α) below in each of the above general formula (G1), the above general formula (G1-1), and the above general formula (G1-2), the general formula (α) is any one of the structural formula (α-1), the structural formula (α-2), the structural formula (α-3), and the structural formula (α-4) below.

(α)

(α-1)

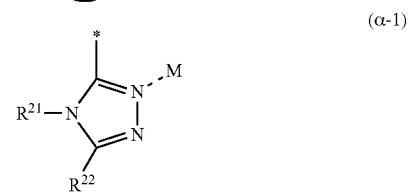

(α-2)

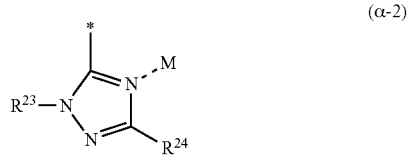

(α-3)

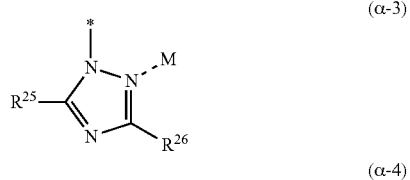

(α-4)

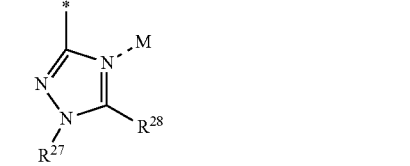

Note that in each of the general formulae (α-1), (α-2), (α-3), and (α-4), each of $R^{21}$ to $R^{28}$ independently represents any of hydrogen, an alkyl group having 1 to 6 carbon atoms, and a substituted or unsubstituted aryl group having 6 to 13 carbon atoms.

Since, in each of the above organometallic complexes which are embodiments of the present invention, one of four types of ligands coordinated to the central metal includes a triazole skeleton including nitrogen bonded to the central metal, energy can be efficiently absorbed, and phosphorescence having an emission spectrum with a peak at around 500 nm can be obtained with high emission quantum efficiency. In the four types of ligands coordinated to the central metal, an indolo[3,2-b]carbazole skeleton whose 6-position is bonded to the central metal or a pyrido[2,3-b:6,5-b'] diindole skeleton whose 6-position is bonded to the central metal; a benzene skeleton whose carbon is bonded to the central metal; and a pyridine skeleton whose nitrogen is bonded to the central metal or a benzene skeleton whose carbon is bonded to the central metal are bonded to one another through nitrogen of an indolo[3,2-b]carbazole skeleton whose 6-position is bonded to the central metal or a pyrido[2,3-b:6,5-b']diindole skeleton whose 6-position is bonded to the central metal, and therefore, the above-described organometallic complex which is one embodiment of the present invention has a rigid structure. Thus, the molecular structure is stabilized and less likely to be distorted, and therefore, the heat resistance can be improved, and the oscillator strength of electron transition between the lowest vibrational levels (0-0 transition) in which transition energy of absorption is equal to that of light emission is increased because a difference between the bond length of atoms in a ground state and the bond length of atoms in an excited state is extremely small, so that an emission spectrum can be further narrowed, and phosphorescence with high color purity can be obtained.

Another embodiment of the present invention is an organometallic complex represented by the structural formula (100) below.

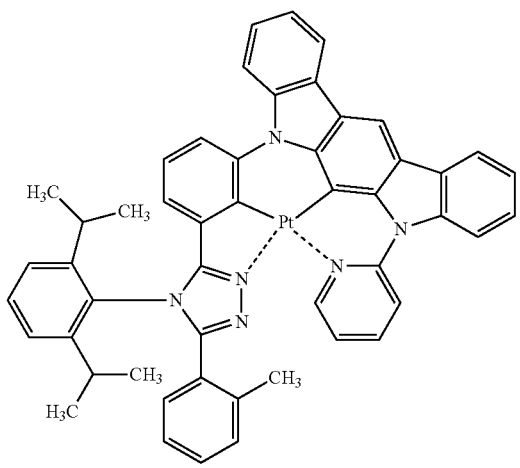

(100)

The organometallic complex which is one embodiment of the present invention is very effective for the following reason: the organometallic complex can emit phosphorescence, that is, it can provide luminescence from a triplet excited state and can exhibit light emission, and therefore higher efficiency is possible when the organometallic complex is used in a light-emitting element. Thus, one embodiment of the present invention also includes a light-emitting element in which the organometallic complex of one embodiment of the present invention is used.

One embodiment of the present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

According to one embodiment of the present invention, a novel organometallic complex can be provided. In particular, a novel organometallic complex emitting light with a short wavelength can be provided. In addition, a novel organometallic complex with a high emission quantum efficiency can be provided. Furthermore, an organometallic complex which achieves improved color purity by a reduction of half width of an emission spectrum can be provided. Furthermore, a novel organometallic complex with an excellent sublimation property can be provided. According to one embodiment of the present invention, a novel organometallic complex that can be used in a light-emitting element can be provided. According to one embodiment of the present invention, a novel organometallic complex that can be used in an EL layer of a light-emitting element can be provided. Note that a new light-emitting element including the novel organometallic complex can be provided. Furthermore, a novel light-emitting device, a novel electronic device, or a novel lighting device can be provided. Note that the description of these effects does not disturb the existence of other effects. One embodiment of the present invention does not necessarily achieve all the effects listed above. Other effects will be apparent from and can be derived from the description of the specification, the drawings, the claims, and the like.

DETAILED DESCRIPTION OF THE INVENTION

Figure 1A:
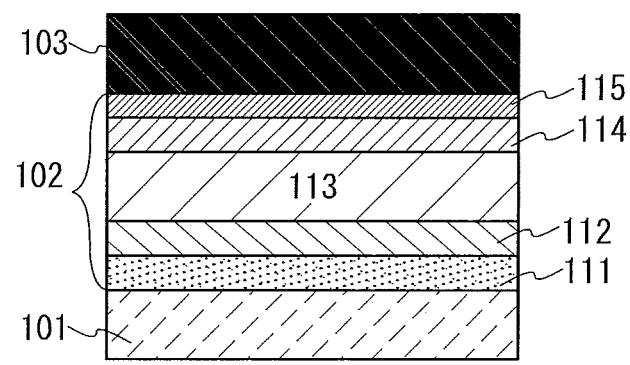
FIGS. 1A and 1B each illustrate a structure of a light-emitting element.

Hereinafter, embodiments of the present invention will be described with reference to the accompanying drawings. Note that the present invention is not limited to the following description, and modes and details thereof can be variously modified without departing from the spirit and scope of the present invention. Therefore, the present invention should not be construed as being limited to the description in the following embodiments.

Note that the terms "film" and "layer" can be interchanged with each other according to circumstances. For example, in some cases, the term "conductive film" can be used instead of the term "conductive layer," and the term "insulating layer" can be used instead of the term "insulating film."

(Embodiment 1)

In this embodiment, organometallic complexes which are embodiments of the present invention will be described.

Each of the organometallic complexes which are described in this embodiment includes a central metal and four types of ligands coordinated to the central metal. The first ligand of the four types of ligands includes a triazole skeleton including nitrogen bonded to the central metal. The second ligand of the four types of ligands includes an indolo[3,2-b]carbazole skeleton whose 6-position is bonded to the central metal or a pyrido[2,3-b:6,5-b']diindole skeleton whose 6-position is bonded to the central metal. The third ligand of the four types of ligands includes a benzene skeleton whose carbon is bonded to the central metal. The fourth ligand of the four types of ligands includes a pyridine skeleton whose nitrogen is bonded to the central metal or a benzene skeleton whose carbon is bonded to the central metal.

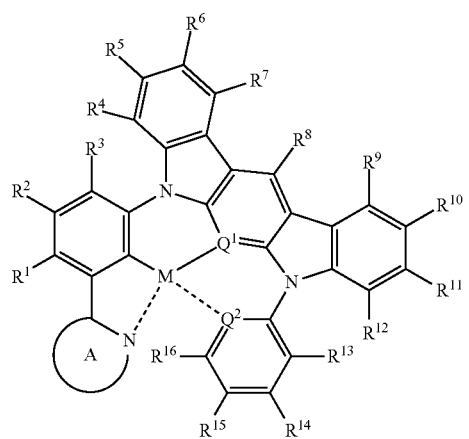

(G1)

In the general formula (G1), M represents Pt or Pd. Each of $R^1$ to $R^{16}$ independently represents any of hydrogen, an alkyl group having 1 to 6 carbon atoms, and a substituted or unsubstituted aryl group having 6 to 13 carbon atoms. One of $Q^1$ and $Q^2$ represents nitrogen, and the other thereof represents carbon. Furthermore, a ring A represents a triazole ring.

Note that in the case where $Q^1$ is nitrogen and $Q^2$ is carbon in the above general formula (G1), an organometallic complex of one embodiment of the present invention is represented by the general formula (G1-1) below. In the case where $Q^1$ is carbon and $Q^2$ is nitrogen in the above general formula (G1), an organometallic complex of one embodiment of the present invention is represented by the general formula (G1-2) below.

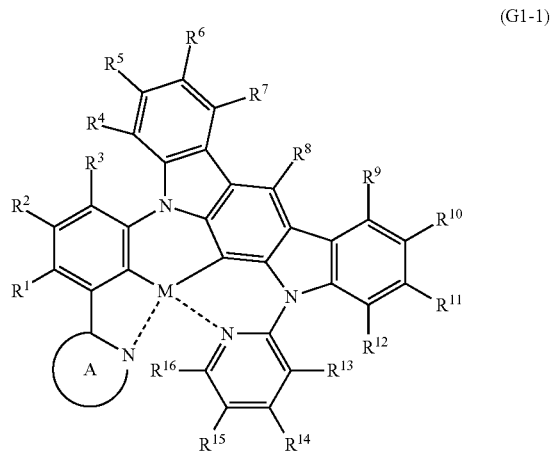

(G1-1)

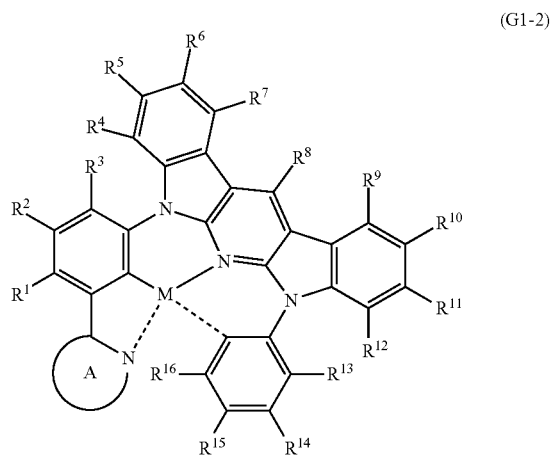

(G1-2)

Note that in each of the general formulae (G1-1) and (G1-2), M represents Pt or Pd. Each of $R^1$ to $R^{16}$ independently represents any of hydrogen, an alkyl group having 1 to 6 carbon atoms, and a substituted or unsubstituted aryl group having 6 to 13 carbon atoms. Furthermore, a ring A represents a triazole ring.

In each of the above general formulae (G1), (G1-1), and (G1-2), the ring A is a triazole ring represented by the general formula (α), and as specific examples thereof, structures represented by the general formulae (α-1), (α-2), (α-3), and (α-4) below can be given.

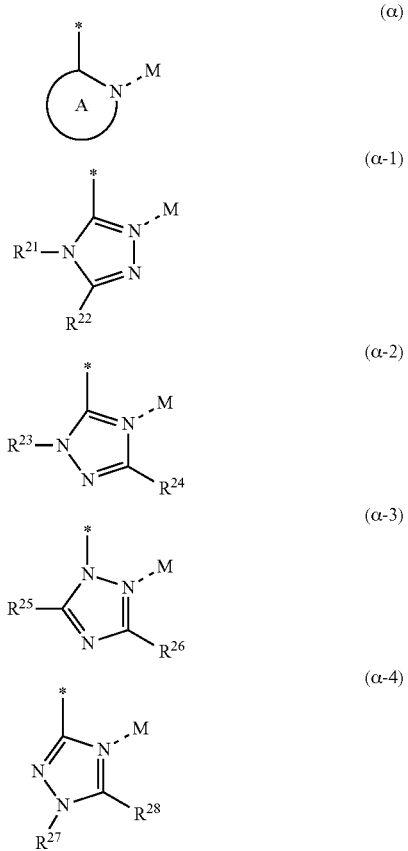

Note that in each of the above general formulae (α-1), (α-2), (α-3), and (α-4), each of $R^{21}$ to $R^{28}$ independently represents any of hydrogen, an alkyl group having 1 to 6 carbon atoms, and a substituted or unsubstituted aryl group having 6 to 13 carbon atoms.

Specific examples of the alkyl group having 1 to 6 carbon atoms in the above general formulae (G1), (G1-1), and (G1-2) and the above general formulae (α-1), (α-2), (α-3), and (α-4) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a 1-methylpentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Specific examples of the substituted or unsubstituted aryl group having 6 to 13 carbon atoms in the above general formulae (G1), (G1-1), and (G1-2) and the above general formulae (α-1), (α-2), (α-3), and (α-4) include a phenyl group, a tolyl group (an o-tolyl group, an m-tolyl group, and a p-tolyl group), a naphthyl group (a 1-naphthyl group and a 2-naphthyl group), a biphenyl group (a biphenyl-2-yl group, a biphenyl-3-yl group, and a biphenyl-4-yl group), a xylyl group, an indenyl group, a fluorenyl group, a phenanthryl group, and an indenyl group. For example, in the case where the aryl group is a 2-fluorenyl group having two phenyl groups at the 9-position as a substituent, the phenyl groups may be bonded to each other to become a spiro-9, 9'-bifluoren-2-yl group.

Since, in each of the organometallic complexes which are embodiments of the present, invention and represented by the above general formulae (G1), (G1-1), and (G1-2), one of four types of ligands coordinated to the central metal includes a triazole skeleton including nitrogen bonded to the central metal, energy can be efficiently absorbed, and phosphorescence having an emission spectrum with a peak at around 500 nm can be obtained with high emission quantum efficiency. In the four types of ligands coordinated to the central metal, an indolo[3,2-b]carbazole skeleton whose 6-position is bonded to the central metal or a pyrido[2,3-b:6,5-b']diindole skeleton whose 6-position is bonded to the central metal; a benzene skeleton whose carbon is bonded to the central metal; and a pyridine skeleton whose nitrogen is bonded to the central metal or a benzene skeleton whose carbon is bonded to the central metal are bonded to one another through nitrogen of an indolo[3,2-b]carbazole skeleton whose 6-position is bonded to the central metal or a pyrido[2,3-b:6,5-b']diindole skeleton whose 6-position is bonded to the central metal, and therefore, the above-described organometallic complex which is one embodiment of the present invention has a rigid structure. Thus, the molecular structure is stabilized and less likely to be distorted, and therefore, the heat resistance can be improved, and the oscillator strength of electron transition between the lowest vibrational levels (0-0 transition) in which transition energy of absorption is equal to that of light emission is increased because a difference between the bond length of atoms in a ground state and the bond length of atoms in an excited state is extremely small, so that an emission spectrum can be further narrowed, and phosphorescence with high color purity can be obtained.

Next, specific structural formulae of the above-described organometallic complexes, each of which is one embodiment of the present invention, are shown below. Note that the present invention is not limited to these examples.

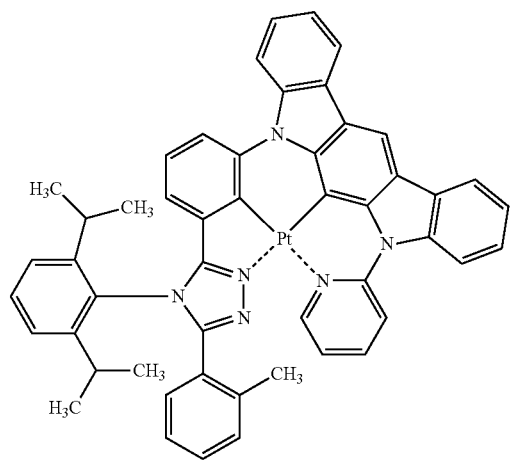

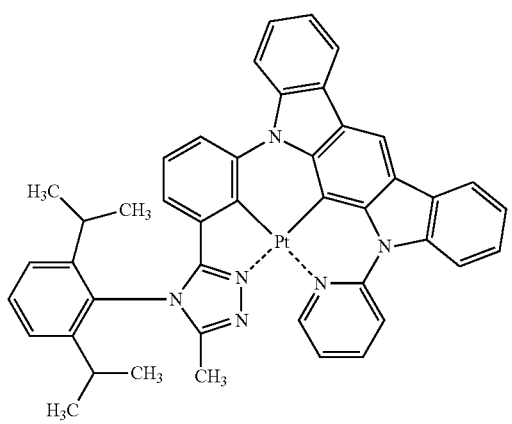
(101)
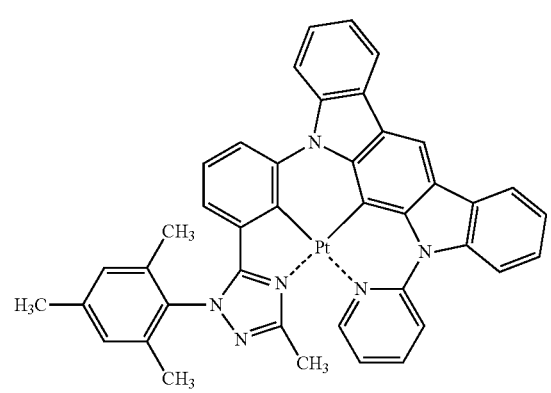
(102)
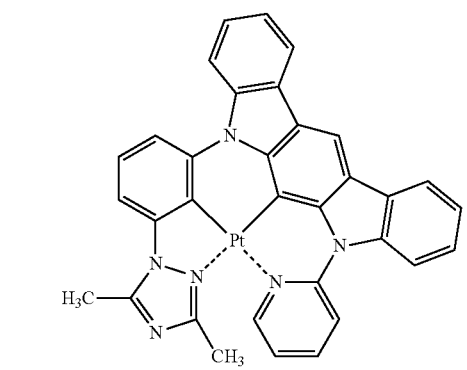
(103)
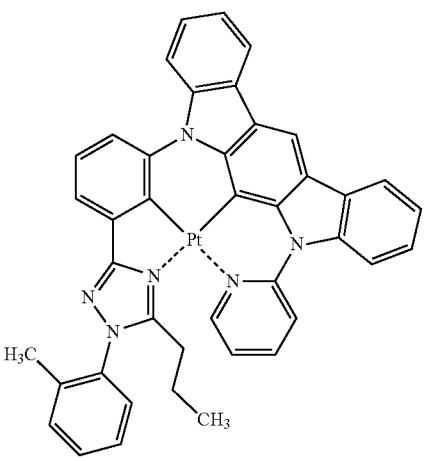
(104)
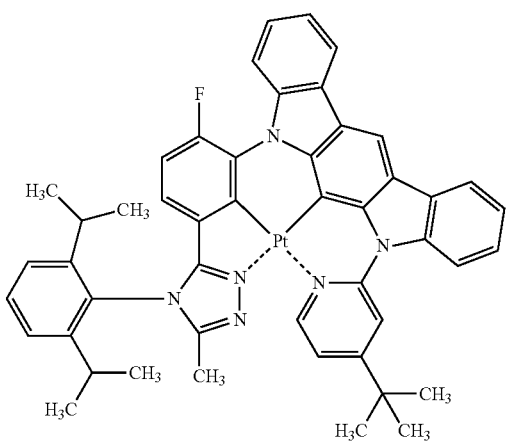
(105)
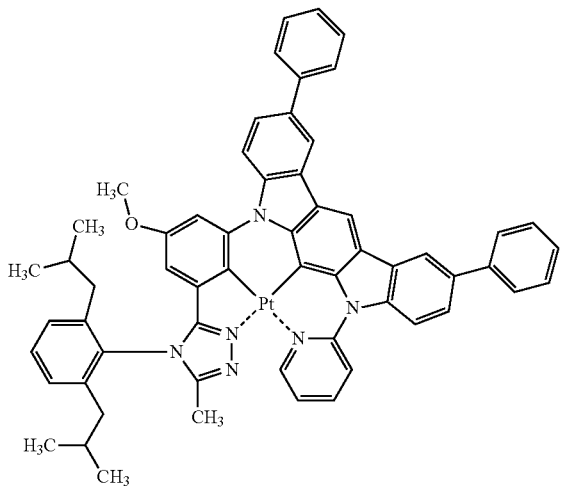
(106)

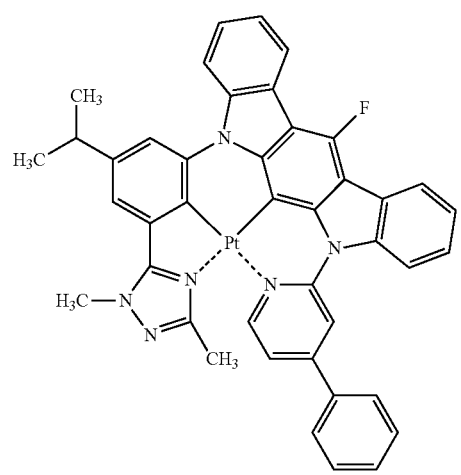
(107)
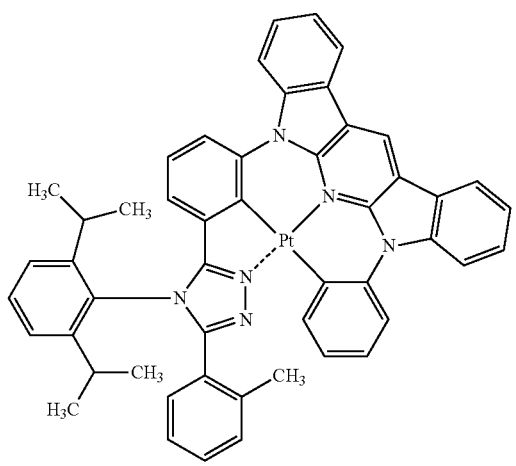
(200)
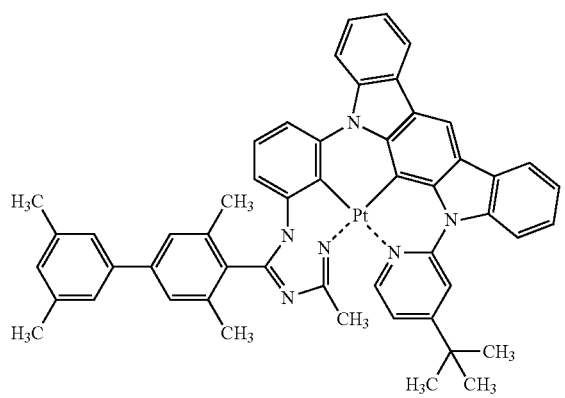
(108)
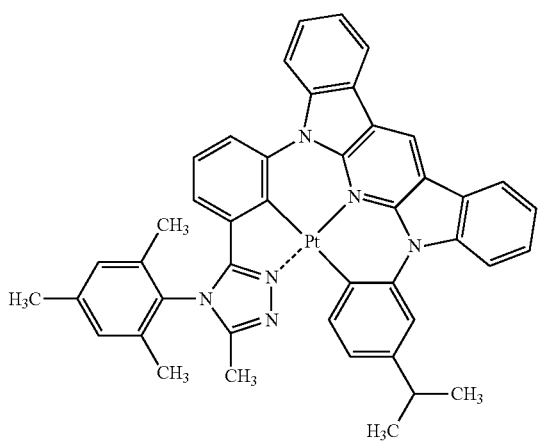
(201)
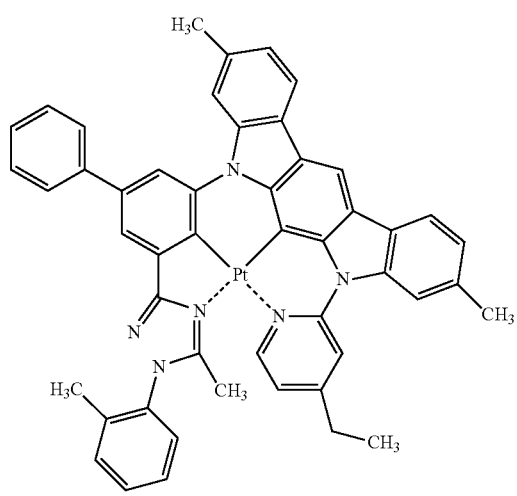
(109)
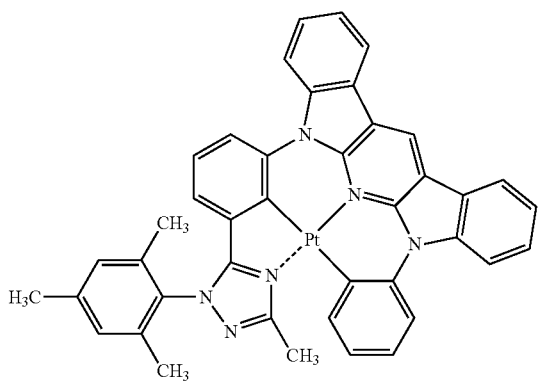
(202)

-continued
(203)
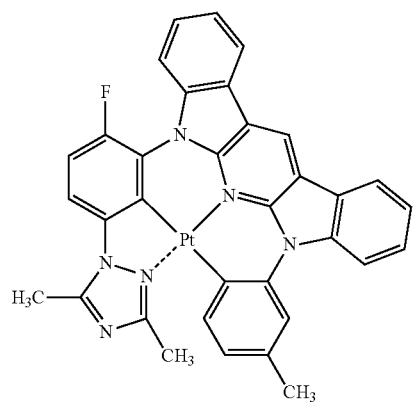
(204)
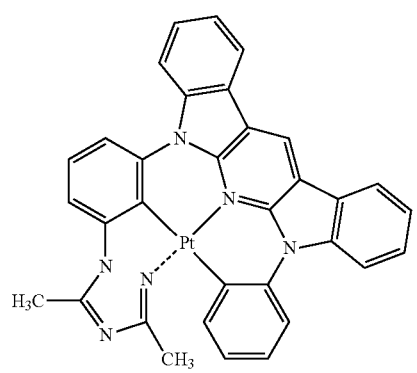
(205)
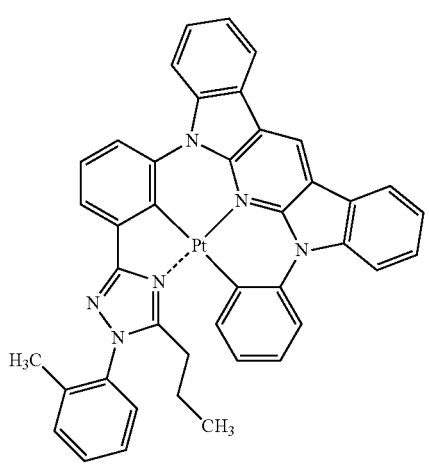
-continued
(301)
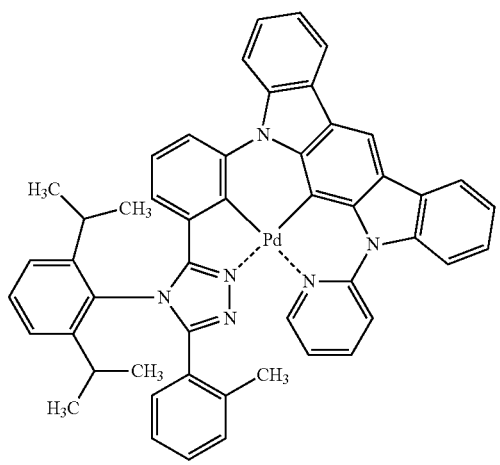
(302)
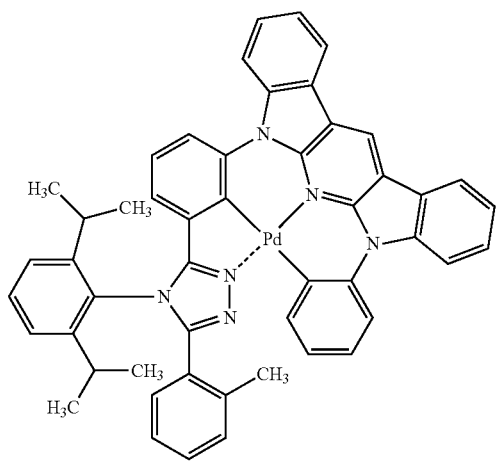
(303)
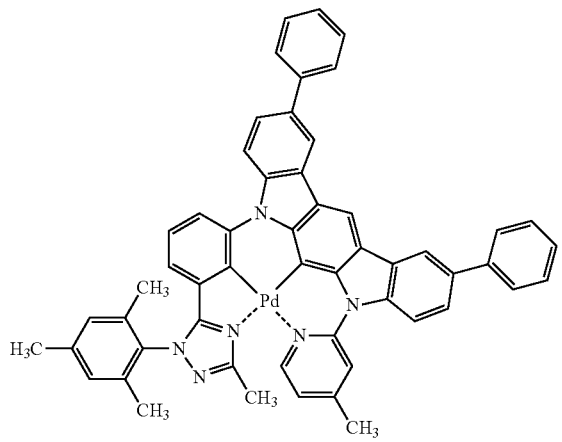

-continued (304)

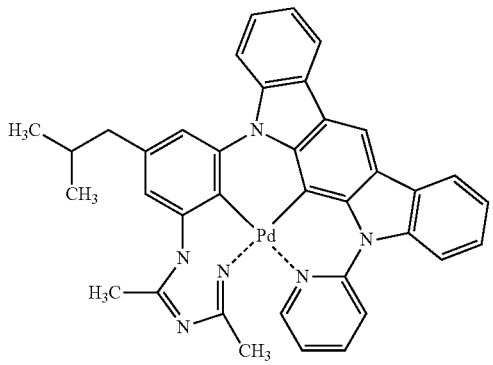

(305)

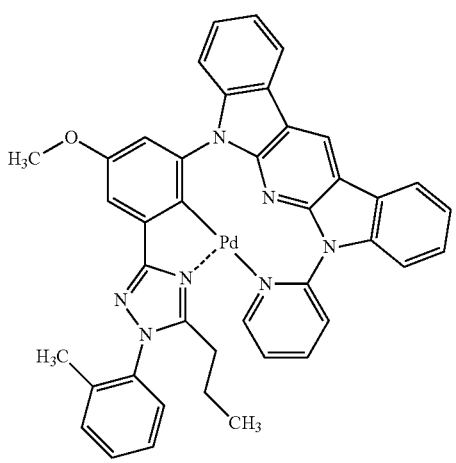

Note that organometallic complexes represented by the structural formulae (100) to (109), (200) to (205), and (301) to (305) are novel substances capable of emitting phosphorescence. Note that there can be geometrical isomers and stereoisomers of these substances depending on the type of the ligand. Each of the organometallic complexes which are embodiments of the present invention includes all of these isomers.

Next, an example of a method of synthesizing the organometallic complex which is one embodiment of the present invention and represented by the above general formula (G1) is described.

<<Synthesis Method of a Derivative Represented by the General Formula (G0)>>

A derivative represented by the general formula (G0) below can be synthesized by a simple synthesis scheme (A) as follows. In the synthesis scheme (A), X represents a halogen.

(G0)

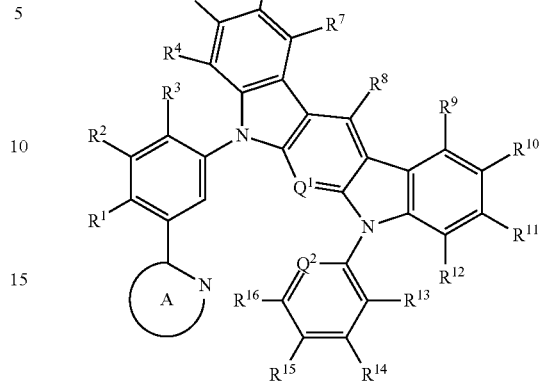

Note that in the general formula (G0), each of $R^1$ to $R^{16}$ independently represents any of hydrogen, an alkyl group having 1 to 6 carbon atoms, and a substituted or unsubstituted aryl group having 6 to 13 carbon atoms, and one of $Q^1$ and $Q^2$ represents nitrogen, and the other thereof represents carbon. Furthermore, a ring A represents a triazole ring.

For example, as shown in the scheme (A) below, the derivative represented by the general formula (G0) can be obtained by coupling of an indolo[3,2-b]carbazole skeleton or a pyrido[2,3-b:6,5-b']diindole skeleton whose 6-position is bonded to the central metal (A1), a halogenated pyridine compound or a halogenated benzene compound (A2), and a halogenated triazole compound (A3).

(A)

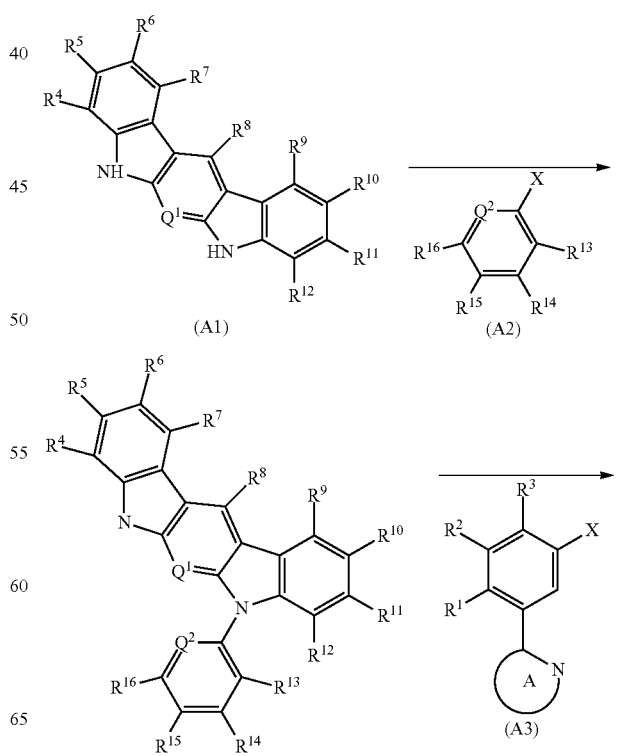

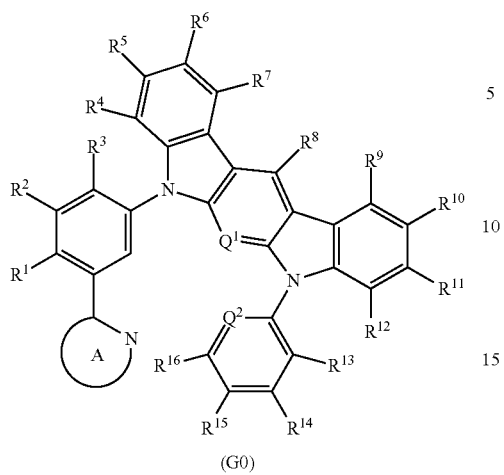

(G0)

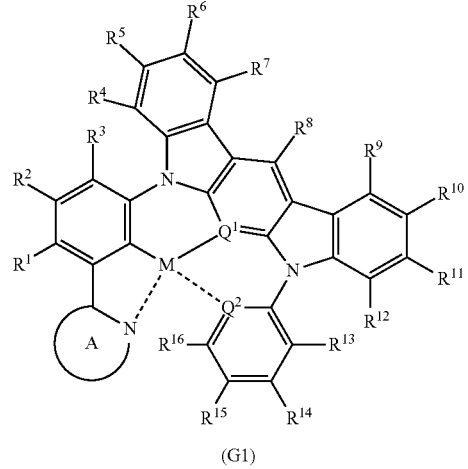

(G1)

A wide variety of the compounds (A1) to (A3) can be obtained or synthesized, and thus a great variety of the derivatives represented by the general formula (G0) can be synthesized. Thus, a feature of the organometallic complex which is one embodiment of the present invention is the abundance of ligand variations.

Next, as shown in a synthesis scheme (B) below, heating is performed in an inert gas atmosphere using the derivative represented by the general formula (G0); palladium including halogen or a metal compound of platinum including halogen (e.g., palladium chloride or potassium tetrachloroplatinate); and acetic acid or a solvent including acetic acid. Thus, the organometallic complex which is one embodiment of the present invention and represented by the general formula (G1) can be obtained.

(B)

palladium including halogen or
metal compound +
of platinum including halogem

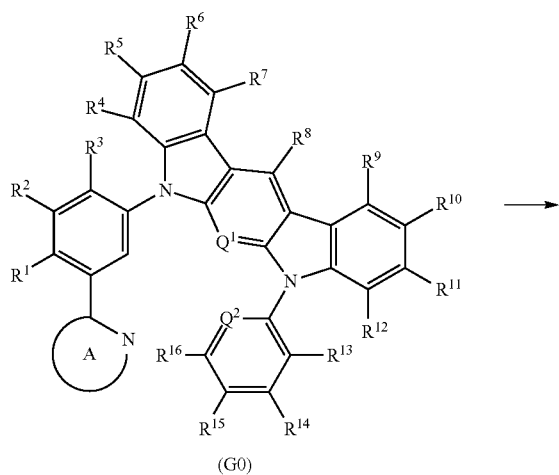

(G0)

In the synthesis scheme (B), M represents Pt or Pd. Each of $R^1$ to $R^{16}$ independently represents any of hydrogen, an alkyl group having 1 to 6 carbon atoms, and a substituted or unsubstituted aryl group having 6 to 13 carbon atoms. One of $Q^1$ and $Q^2$ represents nitrogen, and the other thereof represents carbon. Furthermore, a ring A represents a triazole ring.

The above is the description of the example of a method of synthesizing an organometallic complex which is one embodiment of the present invention; however, the present invention is not limited thereto and any other synthesis method may be employed.

The above-described organometallic complex which is one embodiment of the present invention can emit phosphorescence and thus can be used as a light-emitting material or a light-emitting substance of a light-emitting element.

With the use of the organometallic complex which is one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

In this embodiment, one embodiment of the present invention is described. Other embodiments of the present invention are described in other embodiments. Note that one embodiment of the present invention is not limited thereto. That is, since various embodiments of the present invention are disclosed in this embodiment and the other embodiments, one embodiment of the present invention is not limited to a specific embodiment. The example in which one embodiment of the present invention is applied to a light-emitting element is described; however, one embodiment of the present invention is not limited thereto. Depending on circumstances or conditions, one embodiment of the present invention may be applied to objects other than a light-emitting element.

The structure described in this embodiment can be combined as appropriate with any of the structures described in other embodiments.

(Embodiment 2)

In this embodiment, a light-emitting element which is one embodiment of the present invention will be described with reference to FIGS. 1A and 1B.

In the light-emitting element described in this embodiment, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When a voltage is applied to the light-emitting element, holes injected from the first electrode 101 side and electrons injected from the second electrode 103 side recombine in the light-emitting layer 113; with energy generated by the recombination, a light-emitting substance such as the organometallic complex that is contained in the light-emitting layer 113 emits light.

The hole-injection layer 111 in the EL layer 102 can inject holes into the hole-transport layer 112 or the light-emitting layer 113 and can be formed of, for example, a substance having a high hole-transport property and a substance having an acceptor property, in which case electrons are extracted from the substance having a high hole-transport property by the substance having an acceptor property to generate holes. Thus, holes are injected from the hole-injection layer 111 into the light-emitting layer 113 through the hole-transport layer 112. For the hole-injection layer ill, a substance having a high hole-injection property can also be used. For example, molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

A preferred specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

As the substance having a high hole-transport property which is used for the hole-injection layer 111 and the hole-transport layer 112, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $1 \times 10^{-6}$ cm$^2$/Vs or more is preferably used. The layer formed using the substance having a high hole-transport property is not limited to a single layer and may be formed by stacking two or more layers. Organic compounds that can be used as the substance having a hole-transport property are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like.

Specific examples of carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Other examples are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1 \times 10^{-6}$ cm$^2$/Vs or more and which has 14 to 42 carbon atoms is particularly preferable. The aromatic hydrocarbons may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the substance having an acceptor property which is used for the hole-injection layer 111 and the hole-transport layer 112 are compounds having an electron-withdrawing group (a halogen group or a cyano group) such as 7,7,8,8-tetracyano-2,3,5,6-tetrafluoroquinodimethane (abbreviation: $F_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of hetero atoms, like HAT-CN, is thermally stable and preferable. Oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air and its hygroscopic property is low and is easily treated.

The light-emitting layer 113 contains a light-emitting substance, which may be a fluorescent substance or a phosphorescent substance. In the light-emitting element which is one embodiment of the present invention, the organometallic complex described in Embodiment 1 is preferably used as the light-emitting substance in the light-emitting layer 113. The light-emitting layer 113 preferably contains, as a host material, a substance having higher triplet excitation energy than this organometallic complex (guest material). Alternatively, the light-emitting layer 113 may contain, in addition to the light-emitting substance, two kinds of organic compounds that can form an excited complex (also called an exciplex) at the time of recombination of carriers (electrons and holes) in the light-emitting layer 113 (the two kinds of organic compounds may be any of host materials as described above). In order to form an exciplex efficiently, it is particularly preferable to combine a compound which easily accepts electrons (a material having an electron-transport property) and a compound which easily accepts holes (a material having a hole-transport property). In the case where the combination of a material having an electron-transport property and a material having a hole-transport property which form an exciplex is used as a host material as described above, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing to one side, the reliability of the light-emitting element can be improved.

As the compound that is preferably used to form the above exciplex and easily accepts electrons (material having an electron-transport property), a π-electron deficient heteroaromatic compound such as a nitrogen-containing heteroaromatic compound, a metal complex, or the like can be used. Specific examples include metal complexes such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[a]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)-phenyl]pyrimidine (abbreviation: 4,6mCzP2Pm); a heterocyclic compound having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons, those having triazine skeletons, and those having pyridine skeletons are highly reliable and preferred. In particular, the heterocyclic compounds having diazine (pyrimidine or pyrazine) skeletons and those having triazine skeletons have a high electron-transport property and contribute to a decrease in drive voltage.

As the compound that is preferably used to form the above exciplex and easily accepts holes (the material having a hole-transport property), a π-electron rich heteroaromatic compound (e.g., a carbazole derivative or an indole derivative), an aromatic amine compound, or the like can be favorably used. Specific examples include compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), NPB, N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), BSPB, 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), PCzPCA2, 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), CBP, 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable and have a high hole-transport property and contribute to a reduction in drive voltage.

Note that in the case where the light-emitting layer 113 contains the above-described organometallic complex (guest material) and the host material, phosphorescence with high emission efficiency can be obtained from the light-emitting layer 113.

Figure 1B:
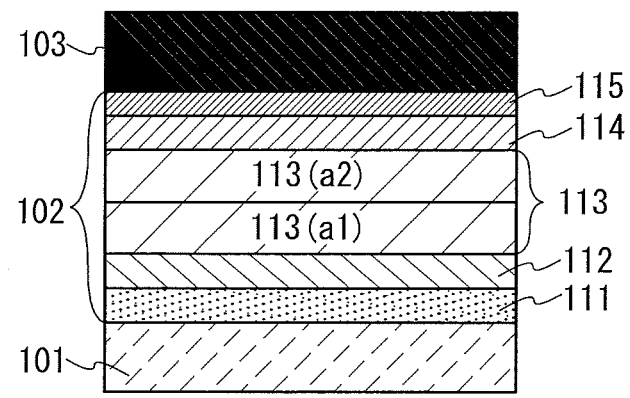

In the light-emitting element, the light-emitting layer 113 does not necessarily have the single-layer structure shown in FIG. 1A and may have a stacked-layer structure including two or more layers as shown in FIG. 1B. In that case, each layer in the stacked-layer structure emits light. For example, fluorescence is obtained from a first light-emitting layer 113(a1), and phosphorescence is obtained from a second light-emitting layer 113(a2) stacked over the first light-emitting layer. Note that the stacking order may be reversed. It is preferable that light emission due to energy transfer from an exciplex to a dopant be obtained from the layer that emits phosphorescence. The emission color of one layer and that of the other layer may be the same or different. In the case where the emission colors are different, a structure in which, for example, blue light from one layer and orange or yellow light or the like from the other layer can be obtained can be formed. Each layer may contain various kinds of dopants.

Note that in the case where the light-emitting layer 113 has a stacked-layer structure, for example, the organometallic complex described in Embodiment 1, a light-emitting substance converting singlet excitation energy into light emission, and a light-emitting substance converting triplet excitation energy into light emission can be used alone or in combination. In that case, the following substances can be used.

As an example of the light-emitting substance converting singlet excitation energy into light emission, a substance which emits fluorescence (a fluorescent compound) can be given.

Examples of the substance emitting fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl 1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

Examples of the light-emitting substance converting triplet excitation energy into light emission are a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $1\times10^{-6}$ seconds or longer, preferably $1\times10^{-3}$ seconds or longer.

Examples of the substance emitting phosphorescence are bis{2-[3',5'-bis(trifluoromethyl)phenyl]pyridinato-N, $C^{2'}$}iridium(III) picolinate (abbreviation: [Ir(CF$_3$ppy)$_2$(pic)], bis[2-(4',6'-difluorophenyl)pyridinato-N,$C^{2'}$]iridium (III) acetylacetonate (abbreviation: FIracac), tris(2-phenylpyridinato)iridium(III) (abbreviation: [Ir(ppy)$_3$]), bis (2-phenylpyridinato)iridium(III) acetylacetonate (abbreviation: [Ir(ppy)$_2$(acac)]), tris(acetylacetonato) (monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N,$C^{2'}$)iridium(III) acetylacetonate (abbreviation: [Ir(dpo)$_2$(acac)]), bis{2-[4'-(perfluorophenyl)phenyl]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium (III) acetylacetonate (abbreviation: [Ir(bt)$_2$(acac)]), bis[2-(2'-benzo[4,5-a]thienyl)pyridinato-N,$C^{3'}$]iridium(III) acetylacetonate (abbreviation: [Ir(btp)$_2$(acac)]), bis(1-phenylisoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato) iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: [Eu(DBM)$_3$(Phen)]), tris[1-(2-thenoyl)-3,3,3-trifluoroacetonato](monophenanthroline)europium(III) (abbreviation: [Eu(TTA)$_3$(Phen)]), and the like.

Examples of the TADF material are fullerene, a derivative thereof, an acridine derivative such as proflavine, eosin, and the like. Other examples are a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin are a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), an octaethylporphyrin-platinum chloride complex (PtCl$_2$OEP), and the like. Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the S1 level and the T1 level becomes small.

The electron-transport layer 114 is a layer containing a substance having a high electron-transport property (also referred to as an electron-transport compound). For the electron-transport layer 114, a metal complex such as tris (8-quinolinolato)aluminum (abbreviation: Alq$_3$), tris(4-methyl-8-quinolinolato)aluminum (abbreviation: Almq$_3$), BeBq$_2$, BAlq, bis[2-(2-hydroxyphenyl)benzoxazolato]zinc (abbreviation: Zn(BOX)$_2$, or bis[2-(2-hydroxyphenyl)benzothiazolato]zinc (abbreviation: Zn(BTZ)$_2$) can be used. Alternatively, a heteroaromatic compound such as PBD, 1,3-bis[5-(p-tert-butylphenyl)-1,3,4-oxadiazol-2-yl]benzene (abbreviation: OXD-7), TAZ, 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly [(9,9-dioctylfluorene-2,7-diyl)-co-(2,2'-bipyridine-6,6'-diyl)] (abbreviation: PF-BPy) can also be used. The substances listed here are mainly ones that have an electron mobility of $1\times10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that each of the hole-injection layer 111, the hole-transport layer 112, the light-emitting layer 113, the electron-transport layer 114, and the electron-injection layer 115 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like. Besides the above-mentioned materials, an inorganic compound such as a quantum dot or a high molecular compound (e.g., an oligomer, a dendrimer, or a polymer) may be used for the hole-injection layer 111, the hole-transport layer 112, the light-emitting layer 113, the electron-transport layer 114, and the electron-injection layer 115, which are described above.

In the above-described light-emitting element, current flows due to a potential difference applied between the first electrode 101 and the second electrode 103 and holes and electrons recombine in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The above-described light-emitting element can emit phosphorescence originating from the organometallic complex and thus can have higher efficiency than a light-emitting element using only a fluorescent compound.

The structure described in this embodiment can be used in appropriate combination with the structure described in any of other embodiments.

(Embodiment 3)

In this embodiment, a light-emitting element (hereinafter referred to as a tandem light-emitting element) which is one embodiment of the present invention and includes a plurality of EL layers is described.

Figure 2A:
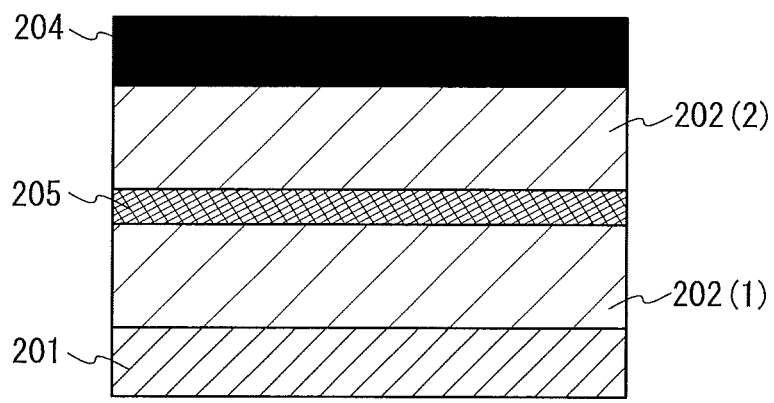
FIGS. 2A and 2B each illustrate a structure of a light-emitting element.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same as or different from each other. When the structures are the same, Embodiment 2 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 2 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $1 \times 10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: $F_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air and its hygroscopic property is low and is easily treated.

In the case of the structure in which an electron donor is added to an organic compound having a high electron-transport property, as the organic compound having a high electron-transport property, the substances having a high electron-transport property which are given in Embodiment 2 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $1 \times 10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that foci ling the charge-generation layer 205 by using any of the above materials can suppress a drive voltage increase caused by the stack of the EL layers. The charge-generation layer 205 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like.

Figure 2B:
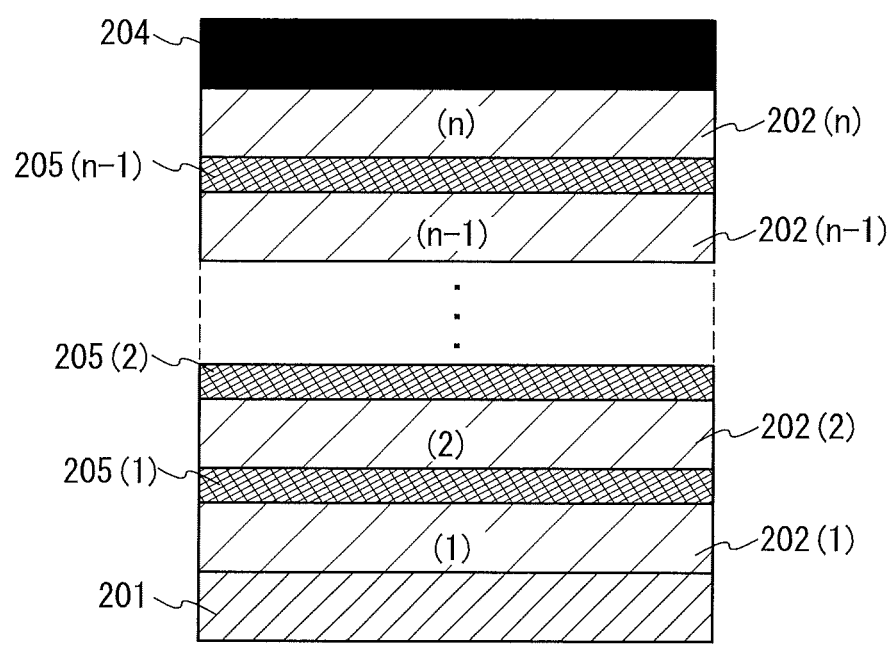

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in other embodiments.

(Embodiment 4)

In this embodiment, a light-emitting device which is one embodiment of the present invention is described.

The light-emitting device may be either a passive matrix light-emitting device or an active matrix light-emitting device. Any of the light-emitting elements described in other embodiments can be used for the light-emitting device described in this embodiment.

In this embodiment, first, an active matrix light-emitting device is described with reference to FIGS. 3A to 3C.

Figure 3A:
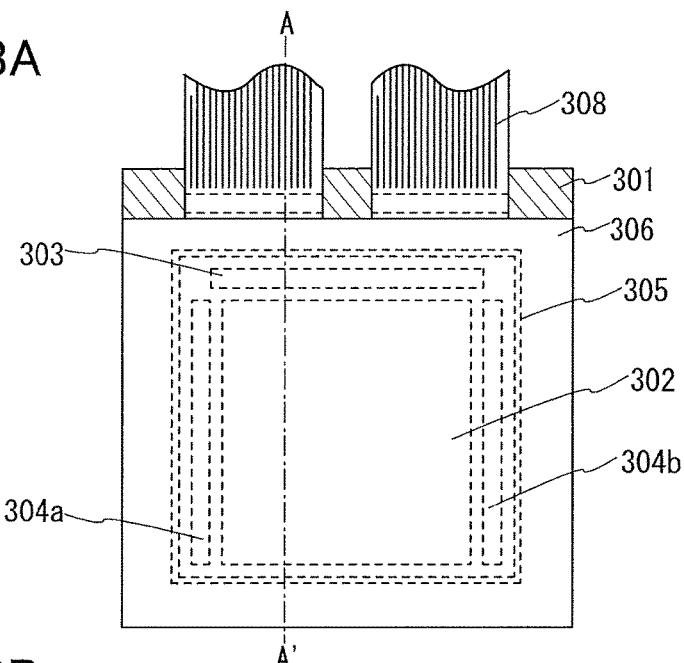
FIGS. 3A to 3C illustrate a light-emitting device.
Figure 3B:
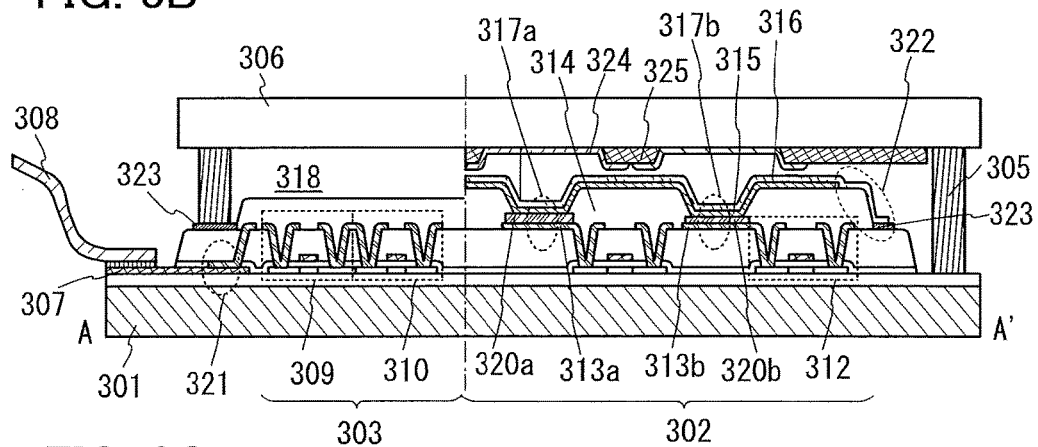

Note that FIG. 3A is a top view illustrating a light-emitting device and FIG. 3B is a cross-sectional view taken along the chain line A-A' in FIG. 3A. The active matrix light-emitting device includes a pixel portion 302 provided over an element substrate 301, a driver circuit portion (a source line driver circuit) 303, and driver circuit portions (gate line driver circuits) 304a and 304b. The pixel portion 302, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or an potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not shown) and a current control FET 312, and a wiring of the current control FET 312 (a source electrode or a drain electrode) is electrically connected to first electrodes (anodes) (313a and 313b) of light-emitting elements 317a and 317b. Although the pixel portion 302 includes two FETs (the switching FET and the current control FET 312) in this embodiment, one embodiment of the present invention is not limited thereto. The pixel portion 302 may include, for example, three or more FETs and a capacitor in combination.

As the FETs 309, 310, and 312, for example, a staggered transistor or an inverted staggered transistor can be used. Examples of a semiconductor material that can be used for the FETs 309, 310, and 312 are a Group 13 semiconductor, a Group 14 semiconductor (e.g., silicon), a compound semiconductor, an oxide semiconductor, and an organic semiconductor. In addition, there is no particular limitation on the crystallinity of the semiconductor material, and an amorphous semiconductor or a crystalline semiconductor can be used. In particular, an oxide semiconductor is preferably used for the FETs 309, 310, 311, and 312. Examples of the oxide semiconductor are In—Ga oxides, In-M-Zn oxides (M is Al, Ga, Y, Zr, La, Ce, Hf, or Nd), and the like. For example, an oxide semiconductor that has an energy gap of 2 eV or more, preferably 2.5 eV or more, further preferably 3 eV or more is used, so that the off-state current of the transistors can be reduced.

In addition, conductive films (320a and 320b) for optical adjustment are stacked over the first electrodes 313a and 313b. For example, as illustrated in FIG. 3B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as anodes in this embodiment.

The insulator 314 preferably has a curved surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked layer structure described in Embodiments 2 and 3. Furthermore, the structure may differ between the light-emitting elements.

For the first electrode 313, the EL layer 315, and the second electrode 316, any of the materials given in Embodiment 2 can be used. The first electrodes (313a and 313b) of the light-emitting elements (317a and 317b) are electrically connected to a lead wiring 307 in a region 321, so that an external signal is input through the FPC 308. The second electrode 316 in the light-emitting elements (317a and 317b) is electrically connected to a lead wiring 323 in a region 322, so that an external signal is input through the FPC 308 that is not illustrated in the figure.

Although the cross-sectional view in FIG. 3B illustrates only the two light-emitting elements 317, a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g. (R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements 317 are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of UV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, an acrylic resin, or the like can be used. In the case where glass frit is used as the sealant, the element substrate 301 and the sealing substrate 306 are preferably glass substrates for high adhesion.

Figure 3C:
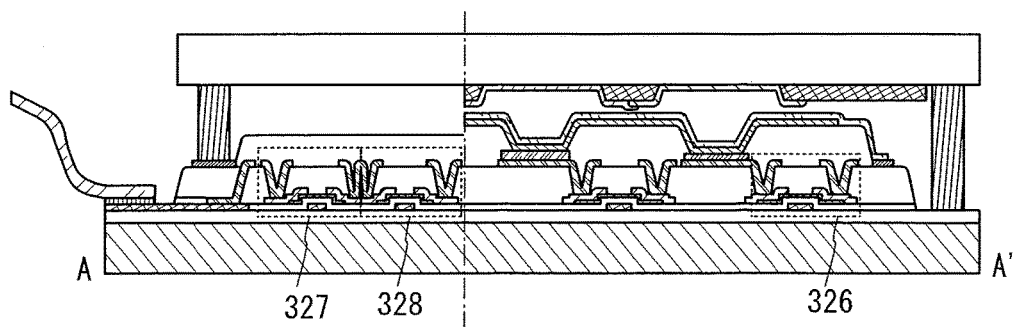

Structures of the FETs electrically connected to the light-emitting elements may be different from those in FIG. 3B in the position of a gate electrode; that is, the structures may be the same as those of a FET 326, a FET 327, and a FET 328, as illustrated in FIG. 3C. The coloring layer (color filter) 324 with which the sealing substrate 306 is provided may be provided as illustrated in FIG. 3C such that, at a position where the coloring layer (color filter) 324 overlaps with the black layer (black matrix) 325, the coloring layer (color filter) 324 further overlaps with an adjacent coloring layer (color filter) 324.

As described above, the active matrix light-emitting device can be obtained.

The light-emitting device which is one embodiment of the present invention may be of the passive matrix type, instead of the active matrix type described above.

Figure 4A:
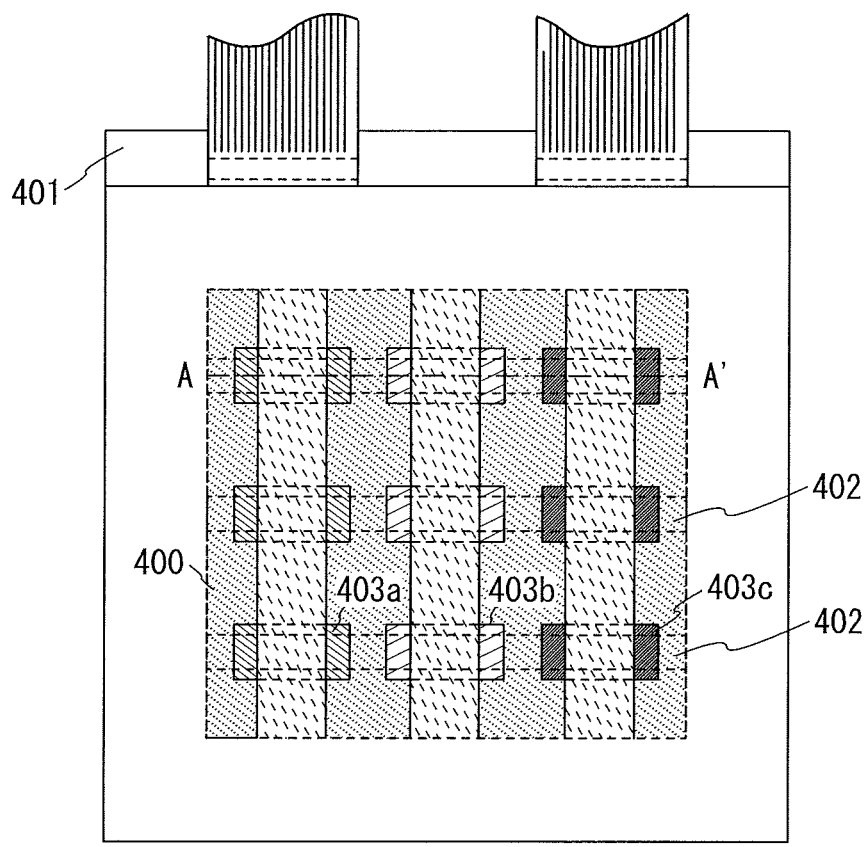
FIGS. 4A and 4B illustrate a light-emitting device.
Figure 4B:
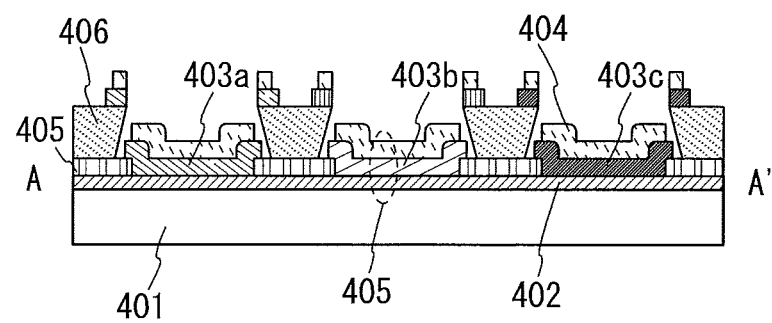

FIGS. 4A and 4B illustrate a passive-matrix light-emitting device. FIG. 4A is a top view of the passive-matrix light-emitting device, and FIG. 4B is a cross-sectional view thereof.

As illustrated in FIG. 4A, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 4A) to form a striped pattern. An insulating film 405 is formed over part of the first electrode 402. A partition 406 formed using an insulating material is provided over the insulating film 405. The sidewalls of the partition 406 slope so that the distance between one sidewall and the other sidewall gradually decreases toward the surface of the substrate as illustrated in FIG. 4B.

Since the insulating film 405 includes openings over the part of the first electrode 402, the EL layers (403a, 403b, and 403c) and second electrodes 404 which are divided as desired can be formed over the first electrode 402. In the example in FIGS. 4A and 4B, a mask such as a metal mask and the partition 406 over the insulating film 405 are employed to form the EL layers (403a, 403b, and 403c) and the second electrodes 404. In this example, the EL layer 403a, the EL layer 403b, and the EL layer 403c emit light of different colors (e.g., red, green, blue, yellow, orange, and white).

After the formation of the EL layers (403a, 403b, and 403c), the second electrodes 404 are formed. Thus, the second electrode 404 is formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves lower power consumption of the circuit or higher integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

Note that the structure described in this embodiment can be combined as appropriate with any of the structures described in other embodiments.

(Embodiment 5)

In this embodiment, examples of a variety of electronic devices and an automobile manufactured using a light-emitting device which is one embodiment of the present invention are described.

Examples of the electronic device including the light-emitting device are television devices (also referred to as TV or television receivers), monitors for computers and the like, cameras such as digital cameras and digital video cameras, digital photo frames, cellular phones (also referred to as portable telephone devices), portable game consoles, portable information terminals, audio playback devices, large game machines such as pachinko machines, and the like. Specific examples of the electronic devices are illustrated in FIGS. 5A to 5D, 5D'-1, and 5D'-2 and FIGS. 6A to 6C.

Figure 5A:
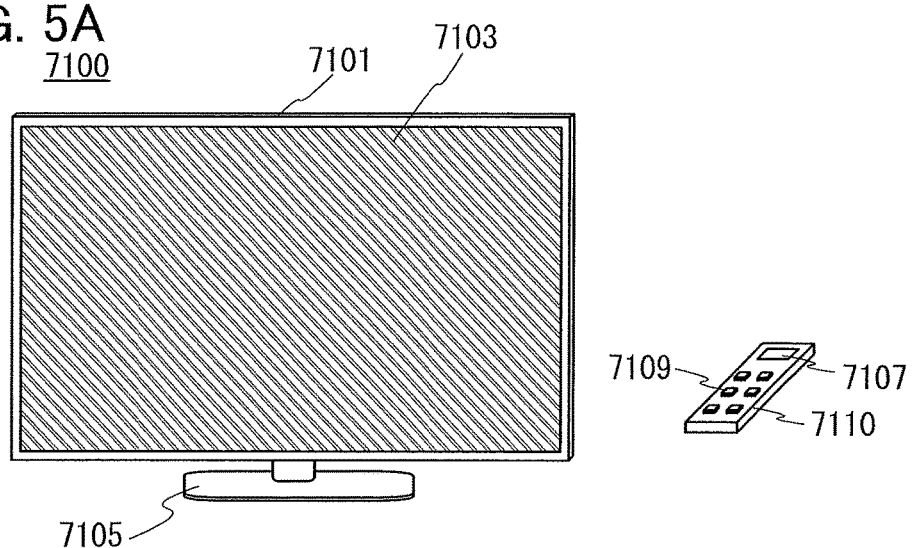
FIGS. 5A to 5E-1 and 5E-2 illustrate electronic devices.

FIG. 5A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 5B:
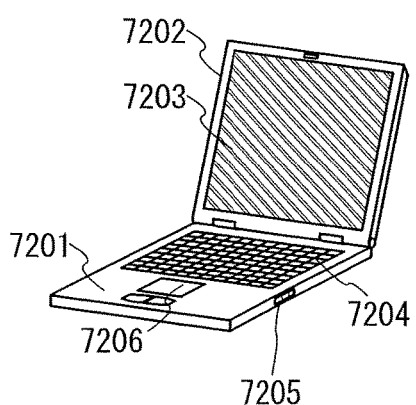

FIG. 5B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 5C:
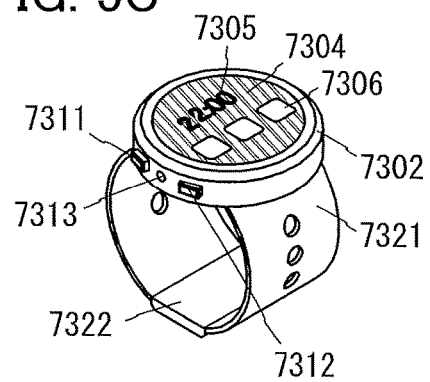

FIG. 5C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 5C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

Figure 5D:
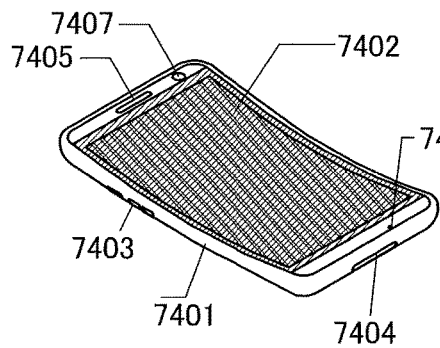
Figures 1, 2, 5E:
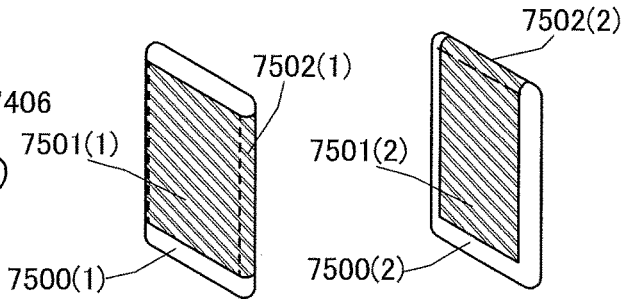

FIGS. 5D, 5D'-1, and 5D'-2 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 5D.

When the display portion 7402 of the cellular phone 7400 illustrated in FIG. 5D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 5D'-1 or FIG. 5D'-2, which is another structure of the cellular phone (e.g., a smartphone).

Note that in the case of the structure illustrated in FIG. 5D'-1 or FIG. 5D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 6A:
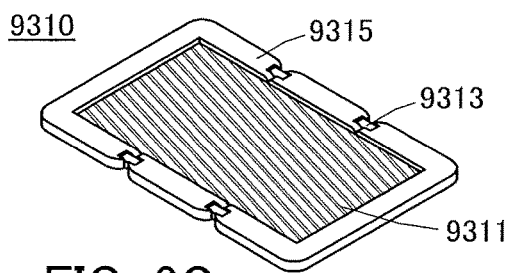
FIGS. 6A to 6C illustrate an electronic device.
Figure 6B:
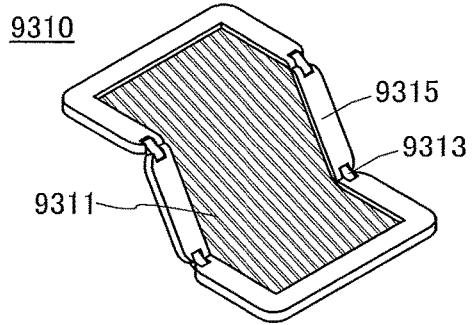
Figure 6C:
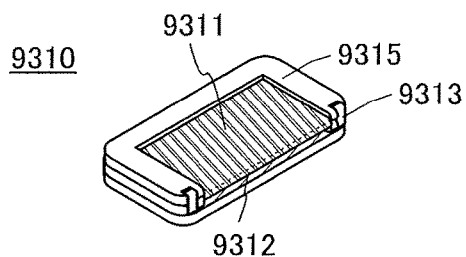

Another electronic device including a light-emitting device is a foldable portable information terminal illustrated in FIGS. 6A to 6C. FIG. 6A illustrates the portable information terminal 9310 which is opened. FIG. 6B illustrates the portable information terminal 9310 which is being opened or being folded. FIG. 6C illustrates the portable information terminal 9310 that is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. A light-emitting device of one embodiment of the present invention can be used for the display portion 9311. A display region 9312 in the display portion 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

Figure 7A:
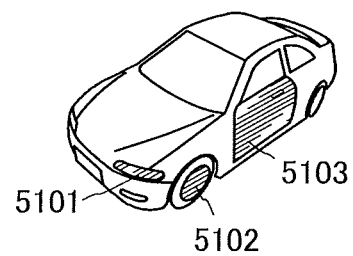
FIGS. 7A and 7B illustrate an automobile.
Figure 7B:
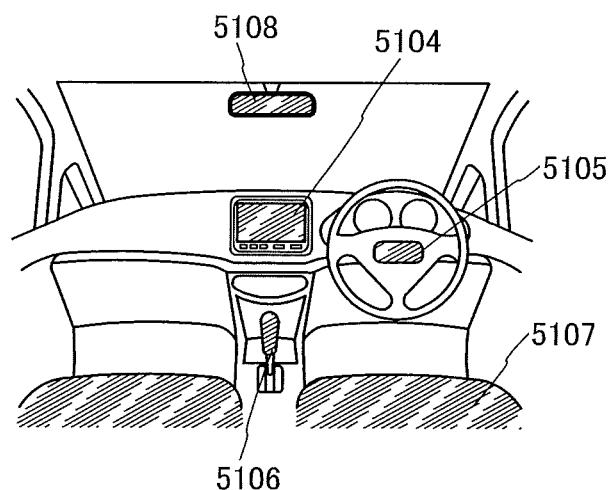

FIGS. 7A and 7B illustrate an automobile including a light-emitting device. The light-emitting device can be incorporated in the automobile, and specifically, can be included in lights 5101 (including lights of the rear part of the car), a wheel 5102 of a tire, a part or whole of a door 5103, or the like on the outer side of the automobile which is illustrated in FIG. 7A. The light-emitting device can also be included in a display portion 5104, a steering wheel 5105, a gear lever 5106, a sheet 5107, a rearview mirror 5108, or the like on the inner side of the automobile which is illustrated in FIG. 7B, or in a part of a glass window.

As described above, the electronic devices and automobiles can be obtained using the light-emitting device which is one embodiment of the present invention. Note that the light-emitting device can be used for electronic devices and automobiles in a variety of fields without being limited to the electronic devices described in this embodiment.

Note that the structure described in this embodiment can be combined as appropriate with any of the structures described in other embodiments.

(Embodiment 6)

In this embodiment, a structure of a lighting device fabricated using the light-emitting element which is one embodiment of the present invention is described with reference to FIGS. 8A to 8D.

Figure 8A:
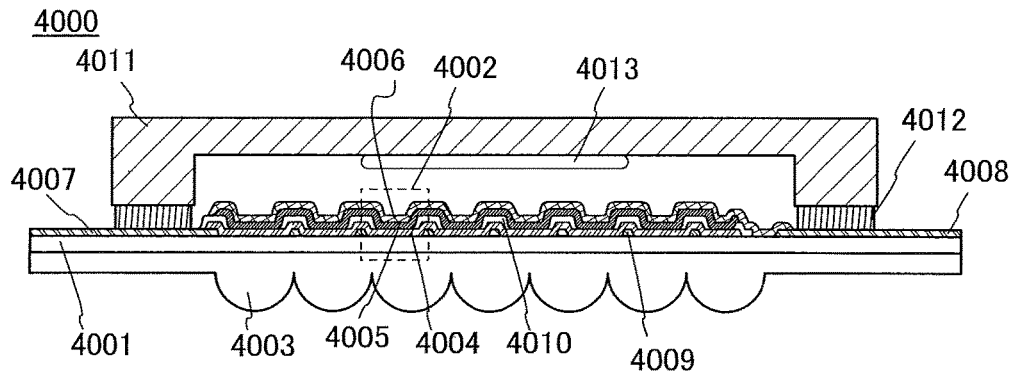
FIGS. 8A to 8D illustrates lighting devices.
Figure 8B:
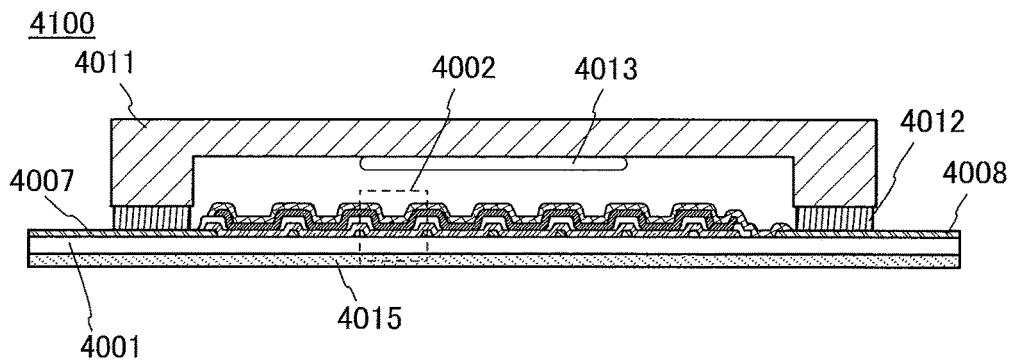
Figure 8C:
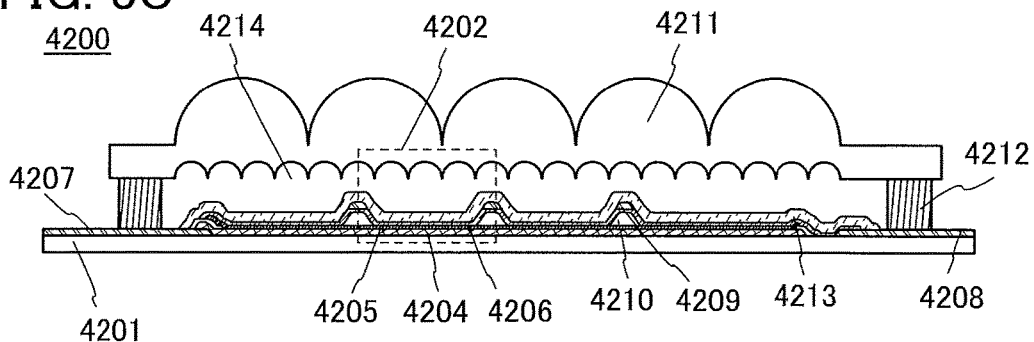
Figure 8D:
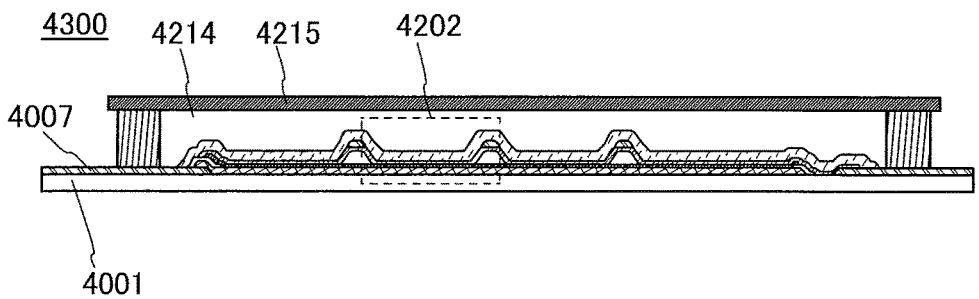

FIGS. 8A to 8D are examples of cross-sectional views of lighting devices. FIGS. 8A and 8B illustrate bottom-emission lighting devices in which light is extracted from the substrate side, and FIGS. 8C and 8D illustrate top-emission lighting devices in which light is extracted from the sealing substrate side.

A lighting device 4000 illustrated in FIG. 8A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 8A, whereby the extraction efficiency of light emitted from the light-emitting element 4002 can be increased.

Instead of the substrate 4003, a diffusion plate 4015 may be provided on the outside of a substrate 4001 as in a lighting device 4100 illustrated in FIG. 8B.

A lighting device 4200 illustrated in FIG. 8C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202. The sealing substrate 4211 has the unevenness illustrated in FIG. 8C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 8D.

Note that the EL layers 4005 and 4205 in this embodiment can include the organometallic complex which is one embodiment of the present invention. In that case, a lighting device with low power consumption can be provided.

Note that the structure described in this embodiment can be combined as appropriate with any of the structures described in other embodiments.

(Embodiment 7)

In this embodiment, examples of a lighting device to which the light-emitting device of one embodiment of the present invention is applied are described with reference to FIG. 9.

Figure 9:
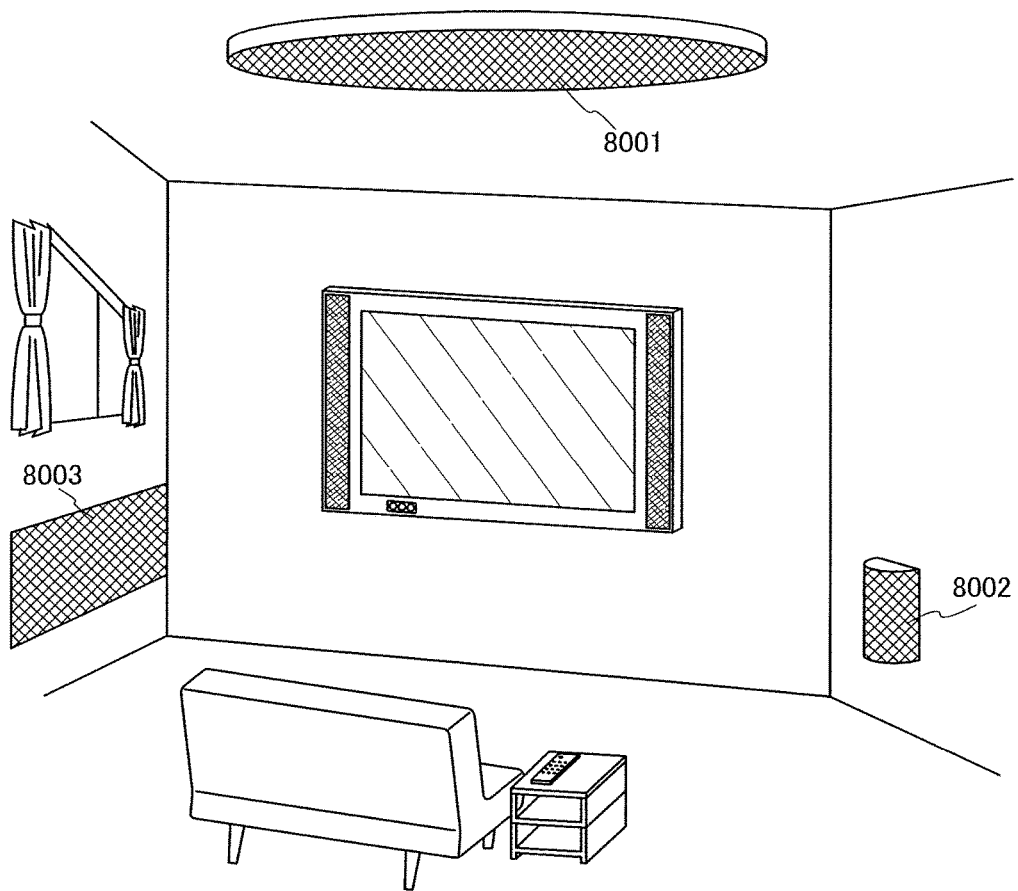
FIG. 9 illustrates lighting devices.

FIG. 9 illustrates an example in which the light-emitting device is used as an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in other embodiments.

(Embodiment 8)

In this embodiment, touch panels including a light-emitting element of one embodiment of the present invention or a light-emitting device of one embodiment of the present invention are described with reference to FIGS. 10A and 10B, FIGS. 11A and 11B, FIGS. 12A and 12B, FIGS. 13A and 13B, and FIG. 14.

Figure 10A:
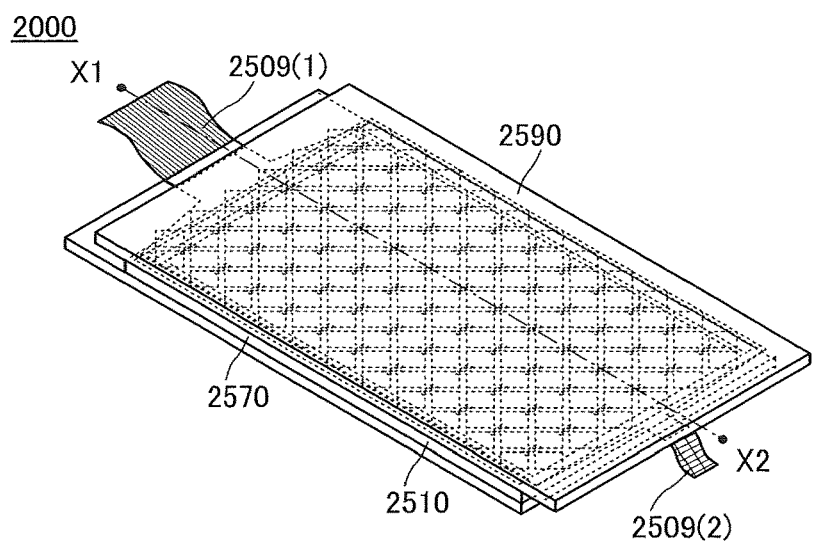
FIGS. 10A and 10B illustrate an example of a touch panel.
Figure 10B:
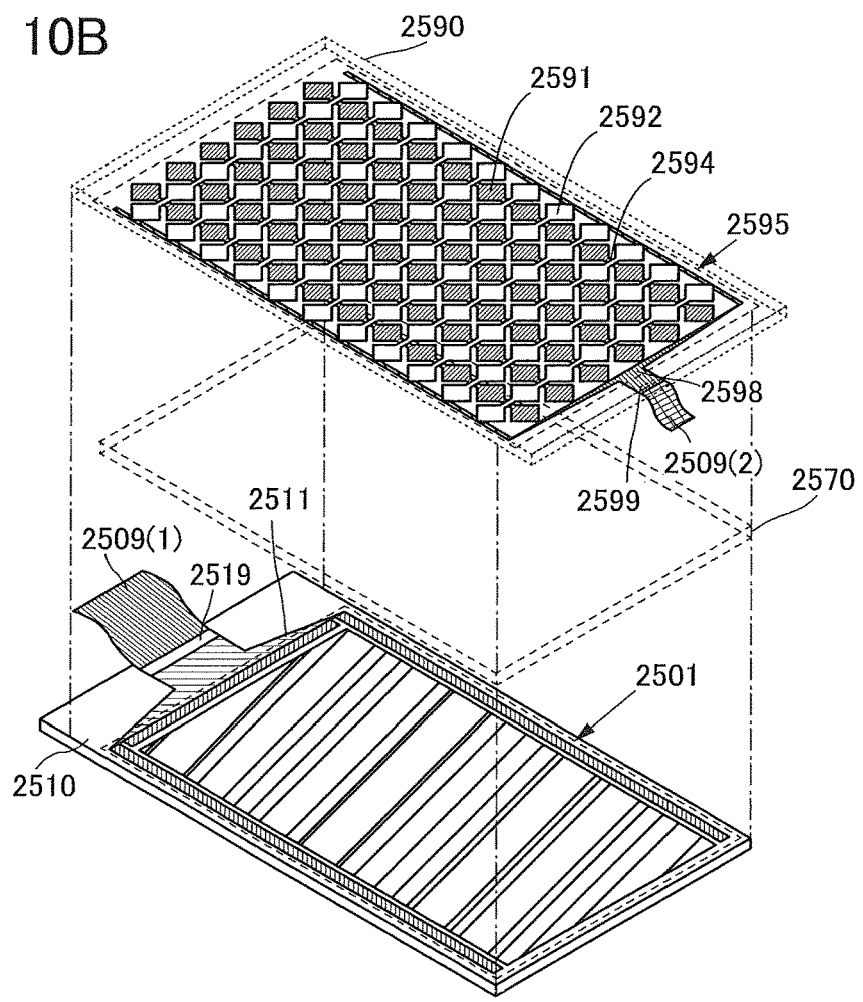

FIGS. 10A and 10B are perspective views of a touch panel 2000. Note that FIGS. 10A and 10B illustrate typical components of the touch panel 2000 for simplicity.

The touch panel 2000 includes a display portion 2501 and a touch sensor 2595 (see FIG. 10B). Furthermore, the touch panel 2000 includes a substrate 2510, a substrate 2570, and a substrate 2590. Note that the substrate 2510, the substrate 2570, and the substrate 2590 each have flexibility.

The display portion 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 10B. Note that in the case of a projected capacitive touch sensor, a variety of sensors that can sense the closeness or the contact of a sensing target such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 10A and 10B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light from the touch sensor 2595 can be reduced.

Note that the shapes of the electrodes 2591 and the electrodes 2592 are not limited to the above-mentioned shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and the electrodes 2592. In that case, between two adjacent electrodes 2592, a dummy electrode which is electrically insulated from these electrodes is preferably provided, whereby the area of a region having a different transmittance can be reduced.

Figure 11A:
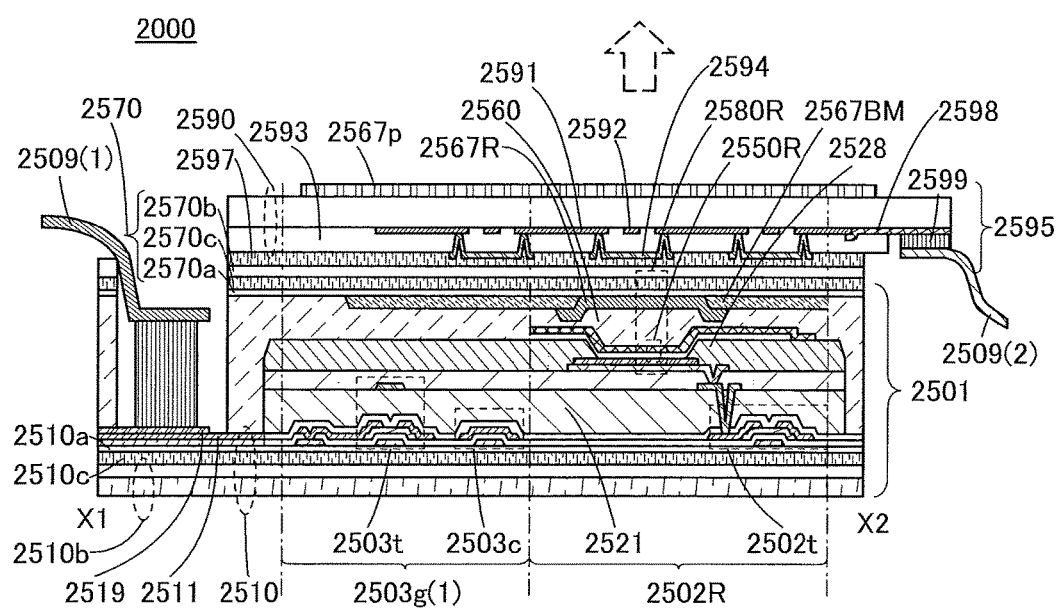
FIGS. 11A and 11B each illustrate an example of a touch panel.
Figure 11B:
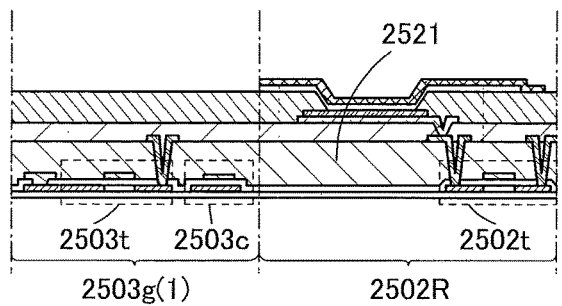

Next, the touch panel 2000 is described in detail with reference to FIGS. 11A and 11B. FIGS. 11A and 11B are cross-sectional views taken along the dashed-dotted line X1-X2 in FIG. 10A.

The touch sensor 2595 includes the electrodes 2591 and the electrodes 2592 that are provided in a staggered arrangement on the substrate 2590, an insulating layer 2593 covering the electrodes 2591 and the electrodes 2592, and the wiring 2594 that electrically connects the adjacent electrodes 2591 to each other.

An adhesive layer 2597 is provided below the wiring 2594. The substrate 2590 is attached to the substrate 2570 with the adhesive layer 2597 so that the touch sensor 2595 overlaps with the display portion 2501.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film containing graphene may be used as well. The film including graphene can be formed, for example, by reducing a film containing graphene oxide. As a reducing method, a method with application of heat or the like can be employed.

For example, the electrodes 2591 and the electrodes 2592 may be formed by depositing a light-transmitting conductive material on the substrate 2590 by a sputtering method and then removing an unnecessary portion by any of various patterning techniques such as a photolithography method.

Examples of a material for the insulating layer 2593 are a resin such as acrylic or epoxy resin, a resin having a siloxane bond, and an inorganic insulating material such as silicon oxide, silicon oxynitride, or aluminum oxide.

The wiring 2594 is formed in an opening provided in the insulating layer 2593, whereby the adjacent electrodes 2591 are electrically connected to each other. A light-transmitting conductive material can be favorably used for the wiring 2594 because the aperture ratio of the touch panel can be increased. Moreover, a material having higher conductivity than the electrodes 2591 and 2592 can be favorably used for the wiring 2594 because electric resistance can be reduced.

Through the wiring 2594, a pair of electrodes 2591 is electrically connected to each other. Between the pair of electrodes 2591, the electrode 2592 is provided.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display portion 2501 includes a plurality of pixels arranged in a matrix. Each of the pixels includes a display element and a pixel circuit for driving the display element.

For the substrate 2510 and the substrate 2570, for example, a flexible material having a vapor permeability of $1\times10^{-5}$ g/(m²·day) or lower, preferably $1\times10^{-6}$ g/(m²·day) or lower can be favorably used. Note that materials whose thermal expansion coefficients are substantially equal to each other are preferably used for the substrate 2510 and the substrate 2570. For example, the coefficient of linear expansion of the materials are preferably lower than or equal to $1\times10^{-3}$/K, further preferably lower than or equal to $5\times10^{-5}$/K, and still further preferably lower than or equal to $1\times10^{-5}$/K.

A sealing layer 2560 preferably has a higher refractive index than the air.

The display portion 2501 includes a pixel 2502R. The pixel 2502R includes a light-emitting module 2580R.

The pixel 2502R includes a light-emitting element 2550R and a transistor 2502*t* which can supply electric power to the light-emitting element 2550R. Note that the transistor 2502*t* functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode.

In the case where the sealing layer 2560 is provided on the light extraction side, the sealing layer 2560 is in contact with the light-emitting element 2550R and the coloring layer 2567R.

The coloring layer 2567R overlaps with the light-emitting element 2550R. Thus, part of light emitted from the light-emitting element 2550R passes through the coloring layer 2567R and is emitted to the outside of the light-emitting module 2580R, as indicated by an arrow in the figure.

The display portion 2501 includes a light-blocking layer 2567BM on the light extraction side. The light-blocking layer 2567BM is provided so as to surround the coloring layer 2567R.

The display portion 2501 includes an anti-reflective layer 2567p in a region overlapping with pixels. As the anti-reflective layer 2567p, a circular polarizing plate can be used, for example.

An insulating layer 2521 is provided in the display portion 2501. The insulating layer 2521 covers the transistor 2502t. With the insulating layer 2521, unevenness caused by the pixel circuit is reduced. The insulating layer 2521 may serve also as a layer for preventing diffusion of impurities. This can prevent a reduction in the reliability of the transistor 2502t or the like due to diffusion of impurities.

The light-emitting element 2550R is formed above the insulating layer 2521. A partition 2528 is provided so as to overlap with end portions of the lower electrode in the light-emitting element 2550R. Note that a spacer for controlling the distance between the substrate 2510 and the substrate 2570 may be provided over the partition 2528.

A scan line driver circuit 2503g(1) includes a transistor 2503t and a capacitor 2503c. Note that the driver circuit and the pixel circuits can be found in the same process over the same substrate.

Over the substrate 2510, the wirings 2511 through which a signal can be supplied are provided. Over the wirings 2511, the terminal 2519 is provided. The FPC 2509(1) is electrically connected to the terminal 2519. The FPC 2509(1) has a function of supplying signals such as an image signal and a synchronization signal. Note that a printed wiring board (PWB) may be attached to the FPC 2509(1).

For the display portion 2501, transistors with a variety of structures can be used. In the example of FIG. 11A, bottom-gate transistors are used. In each of the transistor 2502t and the transistor 2503t illustrated in FIG. 11A, a semiconductor layer including an oxide semiconductor can be used for a channel region. Alternatively, in each of the transistor 2502t and the transistor 2503t, a semiconductor layer including amorphous silicon can be used for a channel region. Further alternatively, in each of the transistor 2502t and the transistor 2503t, a semiconductor layer including polycrystalline silicon which is obtained by a crystallization process such as laser annealing can be used for a channel region.

FIG. 11B illustrates the structure of the display portion 2501 in which top-gate transistors are used.

In the case of a top-gate transistor, a semiconductor layer including polycrystalline silicon, a single crystal silicon film that is transferred from a single crystal silicon substrate, or the like may be used for a channel region as well as the above semiconductor layers that can be used for a bottom-gate transistor.

Next, a touch panel having a structure different from that illustrated in FIGS. 11A and 11B is described with reference to FIGS. 12A and 12B.

Figure 12A:
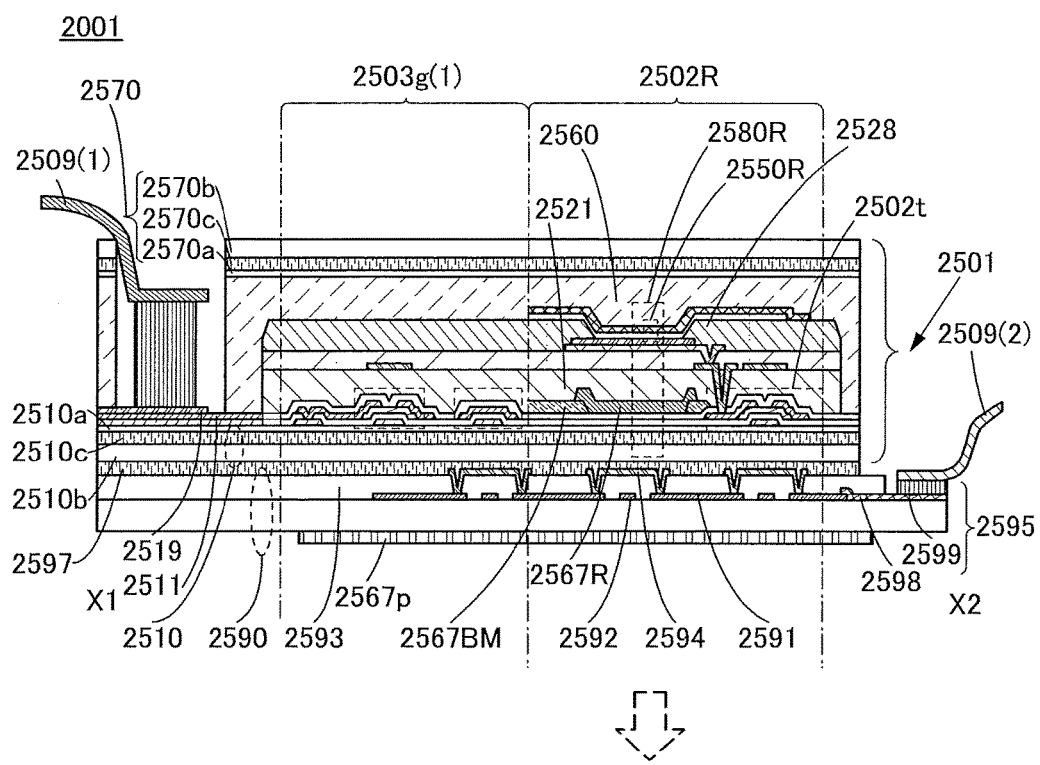
FIGS. 12A and 12B each illustrate an example of a touch panel.
Figure 12B:
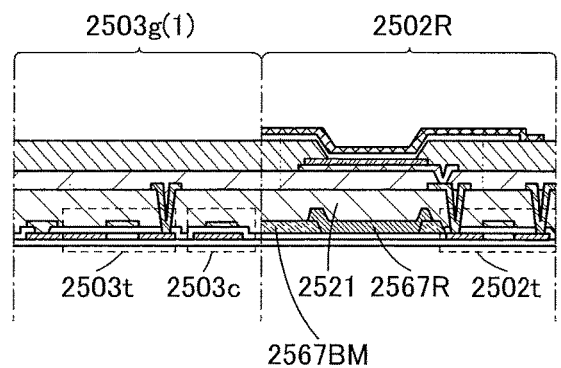

FIGS. 12A and 12B are cross-sectional views of the touch panel 2001. In the touch panel 2001 illustrated in FIGS. 12A and 12B, the position of the touch sensor 2595 relative to the display portion 2501 is different from that in the touch panel 2000 illustrated in FIGS. 11A and 11B. Different structures are described in detail below, and the above description of the touch panel 2000 can be referred to for the other similar structures.

The coloring layer 2567R overlaps with the light-emitting element 2550R. The light-emitting element 2550R illustrated in FIG. 12A emits light to the side where the transistor 2502t is provided. Accordingly, part of light emitted from the light-emitting element 2550R passes through the coloring layer 2567R and is emitted to the outside of the light-emitting module 2580R, as indicated by an arrow in FIG. 12A.

The display portion 2501 includes the light-blocking layer 2567BM on the light extraction side. The light-blocking layer 2567BM is provided so as to surround the coloring layer 2567R.

The touch sensor 2595 is provided on the substrate 2510 side of the display portion 2501 (see FIG. 12A).

The display portion 2501 and the touch sensor 2595 are attached to each other with the adhesive layer 2597 provided between the substrate 2510 and the substrate 2590.

For the display portion 2501, transistors with a variety of structures can be used. In the example of FIG. 12A, a bottom-gate transistor is used. In the example of FIG. 12B, a top-gate transistor is used.

An example of a driving method of the touch panel is described with reference to FIGS. 13A and 13B.

Figure 13A:
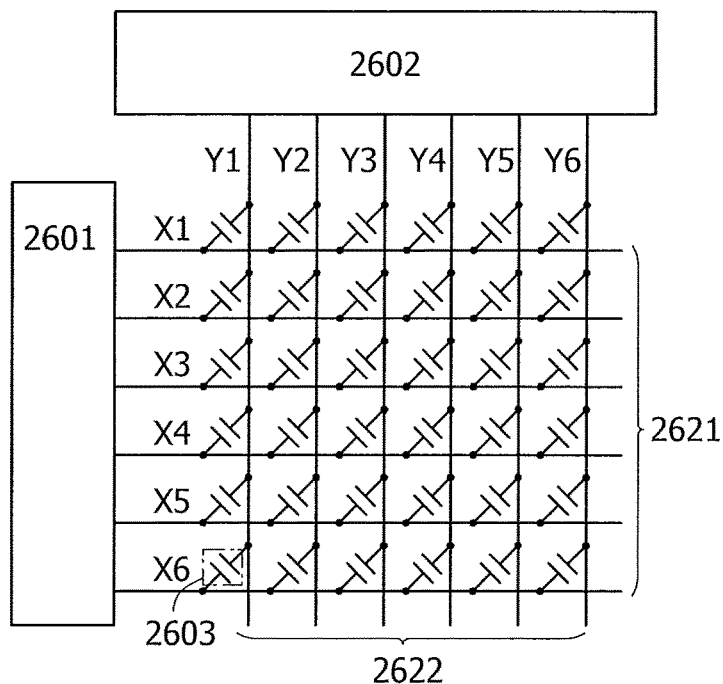
FIGS. 13A and 13B are a block diagram and a timing chart of a touch sensor.

FIG. 13A is a block diagram illustrating the structure of a mutual capacitive touch sensor. FIG. 13A illustrates a pulse voltage output circuit 2601 and a current sensing circuit 2602. Note that in the example of FIG. 13A, six wirings X1-X6 represent electrodes 2621 to which a pulse voltage is supplied, and six wirings Y1-Y6 represent electrodes 2622 that sense a change in current. FIG. 13A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 13B:
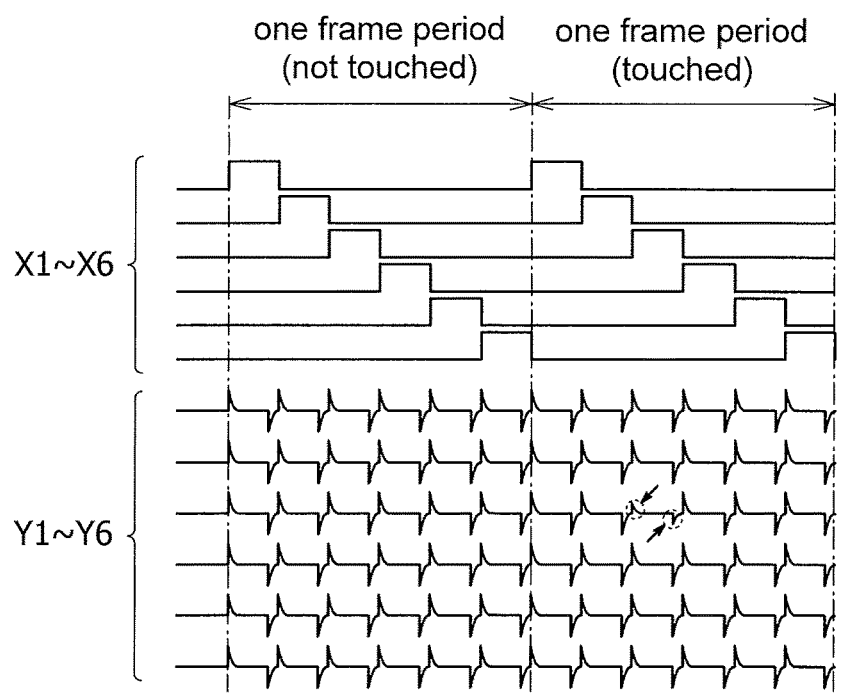

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 14:
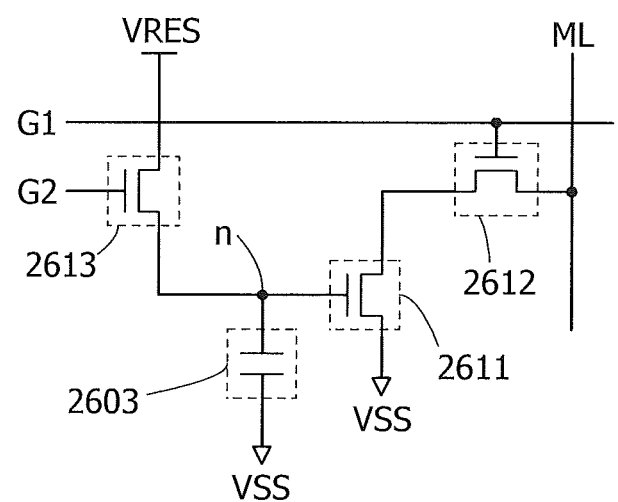
FIG. 14 is a circuit diagram of a touch sensor.

Although FIG. 13A illustrates a passive touch sensor in which only the capacitor 2603 is provided at the intersection of wirings as a touch sensor, an active touch sensor including a transistor and a capacitor may be used. FIG. 14 is a sensor circuit included in an active touch sensor.

The sensor circuit illustrated in FIG. 14 includes the capacitor 2603, a transistor 2611, a transistor 2612, and a transistor 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 14 is described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. Such a transistor is preferably used as the transistor 2613, in particular, so that the potential of the node n can be held for a long time and the frequency of operation of resupplying VRES to the node n (refresh operation) can be reduced.

At least part of this embodiment can be implemented in combination with any of other embodiments described in this specification as appropriate.

EXAMPLE 1

Synthetic Example 1

In this example, a synthesis method of {6-[4-(2,6-diisopropylphenyl)-5-(2-methylphenyl)-4H-1,2,4-triazol-3-yl-κN²)]-[5-(pyridin-2-yl-κN)-5,7-dihydro-indolo[2,3-b]carbazole-5,7-diyl-κC⁶]phenyl-κC}platinum(II) (Abbreviation:[Pt(ptzICz)]) which is an organometallic complex of one embodiment of the present invention represented by the structural formula (100) in Embodiment 1 is described. Note that a structure of [Pt(ptzICz)] is shown below.

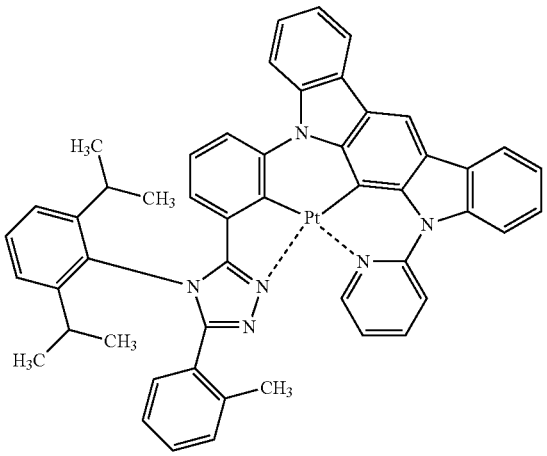

(100)

Step 1: Synthesis of
N-3-bromobenzoyl-N-2-methylbenzoylhydrazide 25.0 g (166 mmol) of o-toluyl hydrazide and 120 mL of N-methyl-2-pyrrolidinone (NMP) were added to a 500-mL three-neck flask. The atmosphere in the flask was replaced with nitrogen. Then, the mixture was stirred while being cooled with ice. To this mixed solution, a mixed solution of 36.5 g (166 mmol) of 3-bromobenzoyl chloride and 50 mL of NMP was slowly added dropwise, and the mixture was stirred for 20 hours. After reaction for the predetermined time, this reacted solution was slowly added to 300 mL of water, so that a white solid was precipitated. The precipitated solid was subjected to ultrasonic cleaning in which water and 1M hydrochloric acid were used alternately. After that, ultrasonic cleaning using ethanol was performed, so that 39.5 g of a white solid was obtained in a yield of 71%. By a nuclear magnetic resonance (NMR) method, the obtained white solid was identified as N-3-bromobenzoyl-N'-2-methylbenzoylhydrazide. The synthesis scheme of Step 1 is shown in (a-0).

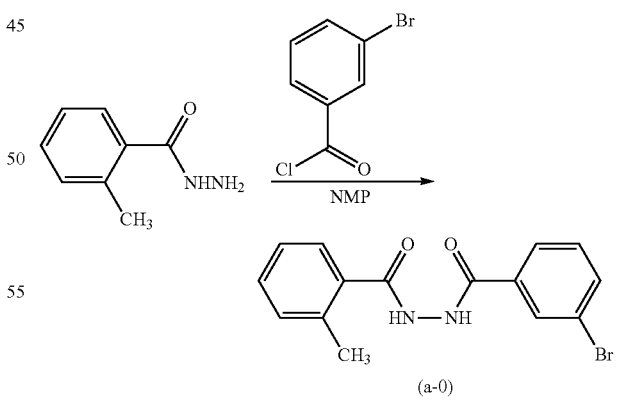

(a-0)

Step 2: Synthesis of N-chloro-3-bromophenylmethylidene-N'-chloro-2-methylphenylmethylidenehydrazone 39.5 g (119 mmol) of N-3-bromobenzoyl-N-2-methylbenzoylhydrazide and 800 mL of toluene were put into a 2000-mL three-neck flask. To this mixed solution, 75.0 g (360 mmol) of phosphorus pentachloride was added and the mixture was heated and stirred at 120° C. for 8 hours under a nitrogen stream. After reaction for the predetermined time, this reacted solution was slowly added to 400 mL of water, and the mixture was stirred at room temperature for 30 minutes. After the stirring, the precipitated solid was removed by filtration, the obtained filtrate was separated to an organic layer and an aqueous layer, and the aqueous layer was extracted with toluene. The extracted solution obtained and the organic layer were collected, the organic layer was slowly added to 400 mL of a 2M potassium hydroxide solution, and the mixture was stirred at room temperature for 48 hours. This mixture was separated to an organic layer and an aqueous layer, and the aqueous layer was extracted with toluene. The obtained solution of the extract and the organic layer were combined and washed with saturated saline. After washing, anhydrous magnesium sulfate was added to the organic layer for drying, and the resulting mixture was subjected to gravity filtration to give a filtrate. The obtained filtrate was concentrated to give an oily substance. The obtained oily substance was purified by silica column chromatography. Toluene was used as a developing solvent. The obtained fraction was concentrated to give 42.6 g of a yellow solid in 97% yield. By a nuclear magnetic resonance (NMR) method, the obtained yellow solid was identified as N-chloro-3-bromophenylmethylidene-N'-chloro-2-methylphenylmethylidenehydrazone. The synthesis scheme of Step 2 is shown in (b-0).

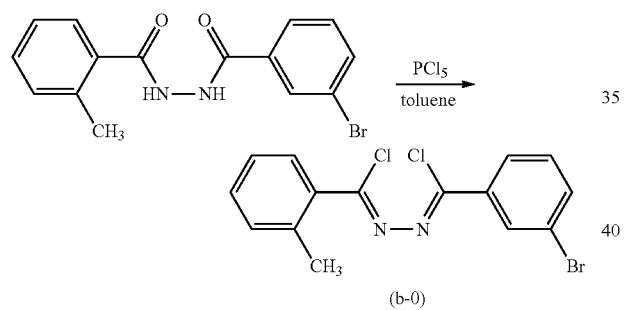

(b-0)

Step 3: Synthesis of 3-(3-bromophenyl)-4-(2,6-diisopropylphenyl)-5-(2-methylphenyl)-4H-1,2,4-triazole 30.0 g (81.0 mmol) of N-chloro-3-bromophenylmethylidene-N'-chloro-2-methylphenylmethylidenehydrazone, 1 g (243 mmol) of 2,6-diisopropylaniline, and 250 mL of N,N-dimethylaniline were put into a 1000-mL three-neck flask, and this mixture was heated and stirred at 160° C. for 13 hours under a nitrogen stream. After reaction for the predetermined time, this reacted solution was put into 3M hydrochloric acid and stirred for 30 minutes. Toluene was added therein, and the aqueous layer was extracted with toluene. The solution of the extract and the organic layer were combined, and washed with water, a saturated aqueous solution of sodium hydrogen carbonate, and saturated saline, and anhydrate magnesium sulfate was added into the organic layer for drying. The obtained mixture was gravity-filtered, and the filtrate was concentrated to give an oily substance. The obtained oily substance was purified by silica column chromatography. As the developing solvent, a 5:1 hexane-ethyl acetate mixed solvent was used. The resulting fraction was concentrated to give a white solid. The solid was recrystallized with a mixed solvent of ethyl acetate and hexane to give 17.6 g of a white solid in a yield of 46%. By a nuclear magnetic resonance (NMR) method, the obtained white solid was identified as 3-(3-bromophenyl)-4-(2,6-diisopropylphenyl)-5-(2-methylphenyl)-4H-1,2,4-triazole. The synthesis scheme of Step 3 is shown in (c-0).

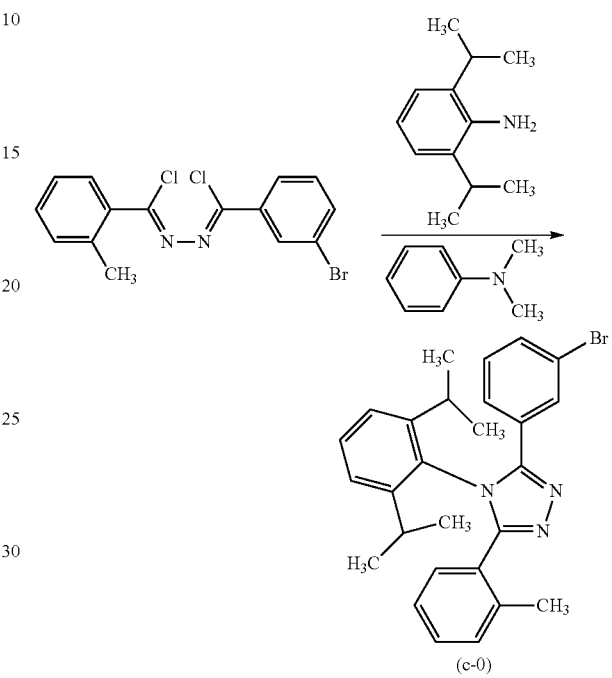

(c-0)

Step 4: Synthesis of 5,7-dihydro-5-(2-pyridyl)-indolo[2,3-b]carbazole 1.0 g (3.9 mmol) of 5,7-dihydro-indolo[2,3-b]carbazole, 0.80 g (3.9 mmol) of 2-iodopyridine, 0.14 g (0.78 mmol) of 1,10-phenanthroline, and 2.5 g (7.8 mmol) of cesium carbonate were put into a reaction container, and the atmosphere in the flask was replaced with nitrogen. 8 mL of N,N-dimethylformamide was added to this mixture, the mixture was stirred to be degassed while the pressure in the flask was reduced. After that, the atmosphere in the flask was replaced with nitrogen, 0.074 g (0.39 mmol) of copper iodide was added, and the mixture was heated at 100° C. for 11.5 hours. Chloroform was added to the reactive mixture and the mixture was subjected to filtration through celite. The obtained filtrate was concentrated to give an oily substance. The obtained oily substance was purified by silica column chromatography. As the developing solvent, a 3:1 hexane-ethyl acetate mixed solvent was used. The obtained fraction was concentrated to obtain a solid. To the obtained solid was added methanol, irradiation with ultrasonic waves was performed, and a solid was removed by suction filtration. The obtained filtrate was concentrated to give 0.37 g of a white solid, which was a target substance, in a yield of 28%. By a nuclear magnetic resonance (NMR) method, the obtained white solid was identified as 5,7-dihydro-5-(2-pyridyl)-indolo[2,3-b]carbazole. The synthesis scheme of Step 4 is shown in (d-0).

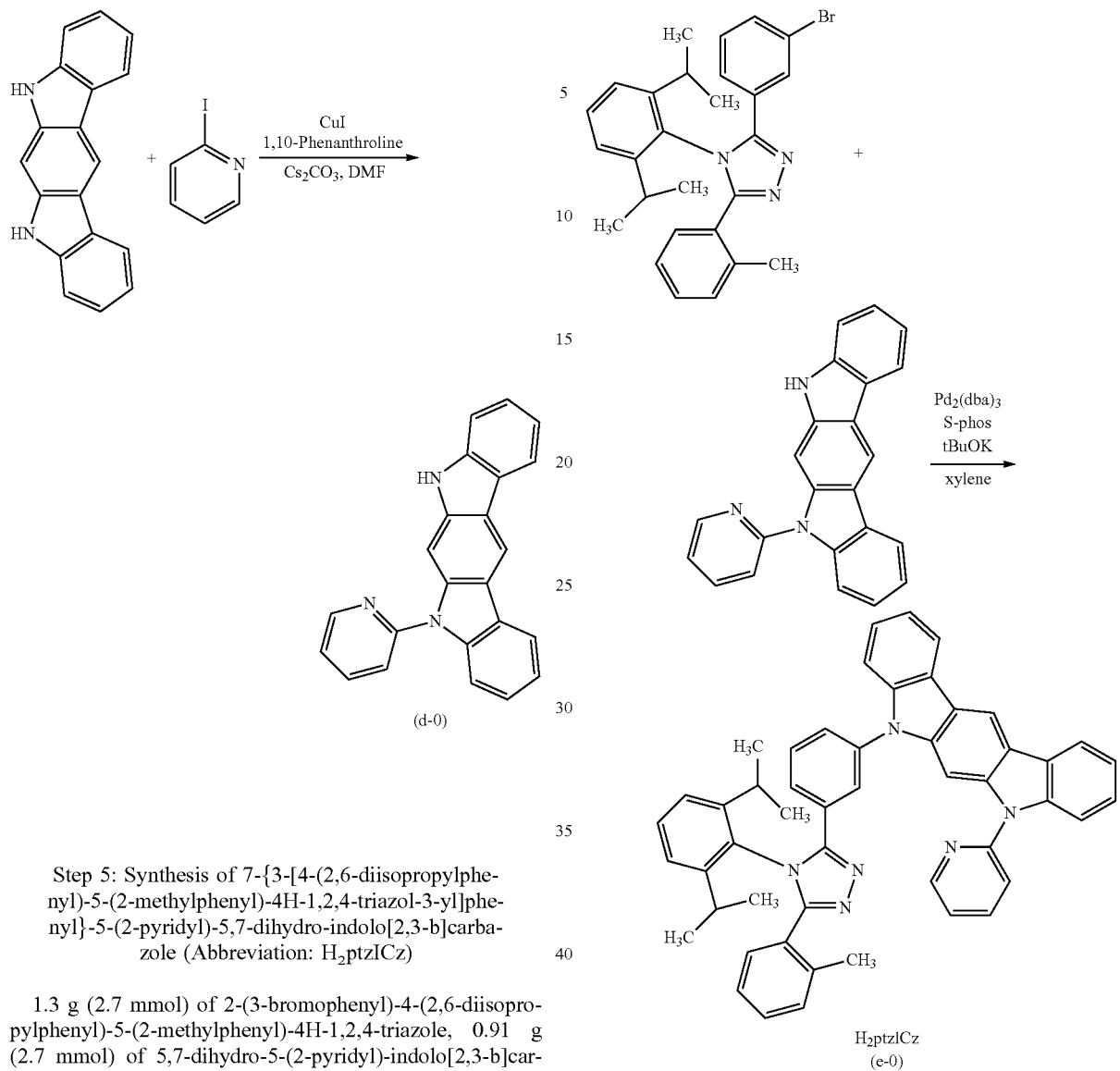

Step 5: Synthesis of 7-{3-[4-(2,6-diisopropylphenyl)-5-(2-methylphenyl)-4H-1,2,4-triazol-3-yl]phenyl}-5-(2-pyridyl)-5,7-dihydro-indolo[2,3-b]carbazole (Abbreviation: H₂ptzICz)

1.3 g (2.7 mmol) of 2-(3-bromophenyl)-4-(2,6-diisopropylphenyl)-5-(2-methylphenyl)-4H-1,2,4-triazole, 0.91 g (2.7 mmol) of 5,7-dihydro-5-(2-pyridyl)-indolo[2,3-b]carbazole, 0.91 g (8.1 mmol) of potassium-tert-butoxide, 0.067 g (0.162 mmol) of 2-dicyclohexylphosphino-2',6'-dimethoxybiphenyl (S-Phos), and 100 mL of xylene were put into a 300-mL three-neck flask, and the atmosphere in the flask was replaced with nitrogen. After that, the mixture was stirred to be degassed while the pressure in the flask was reduced. After that, the atmosphere in the flask was replaced with nitrogen, 0.074 g (0.081 mmol) of tris(dibenzylideneacetone)dipalladium(0) was added, and the mixture was stirred at 120° C. for 7.5 hours under a nitrogen stream. Toluene was added to the reactive mixture and the mixture was subjected to filtration through celite. The obtained filtrate was concentrated to give an oily substance. The obtained oily substance was purified by silica column chromatography. As a developing solvent, a 1:1 hexane-ethyl acetate mixed solvent was used. The obtained fraction was concentrated to give 0.64 g of a white solid in 33% yield. By a nuclear magnetic resonance (NMR) method, the obtained white solid was identified as 7-{3-[4-(2,6-diisopropylphenyl)-5-(2-methylphenyl)-4H-1,2,4-triazol-3-yl]phenyl}-5-(2-pyridyl)-5,7-dihydro-indolo[2,3-b]carbazole. A synthesis scheme of Step 5 is shown in (e-0).

Step 6: Synthesis of {6-[4-(2,6-diisopropylphenyl)-5-(2-methylphenyl)-4H-1,2,4-triazol-3-yl-κN²)]-2-[5-(pyridin-2-yl-κN)-5,7-dihydro-indolo[2,3-b]carbazole-5,7-diyl-κC⁶]phenyl-κC}platinum(II) (Abbreviation: [Pt(ptzICz)])

0.64 g (0.88 mmol) of 7-{3-[4-(2,6-diisopropylphenyl)-5-(2-methylphenyl)-4H-1,2,4-triazol-3-yl)]phenyl}-5-(2-pyridyl)-5,7-dihydro-indolo[2,3-b]carbazole, 0.37 g (0.88 mmol) of potassium chloroplatinate, 0.028 g of (0.088 mmol) of tetrabutylammonium bromide, and 60 mL of glacial acetic acid were put into a 300-mL recovery flask, and this mixture was stirred at 120° C. for 56 hours under a nitrogen stream. 60 mL of water was added to the reactive mixture, and the mixture was stirred for 30 minutes and subjected to suction filtration to give a solid. Tolune was added to the obtained solid and the mixture was filtered through a filter aid in which Celite, alumina, Florisil and Celite were stacked in this order. The obtained filtrate was condensed to obtain a solid. The obtained solid was recrystallized with a mixed solvent of ethyl acetate and hexane to give 0.22 g of an yellow solid in a yield of 27%. 0.21 g of the obtained solid was purified by a train sublimation method. The purification was conducted by heating of the solid at 320° C. for 16 hours under a pressure of 2.6 Pa with a flow rate of argon gas of 5.0 mL/min. After the purification, 0.15 g of [Pt(ptzICz)] which was the object of the synthesis was obtained at a collection rate of 71%. The synthesis scheme of Step 6 is illustrated in (f-0).

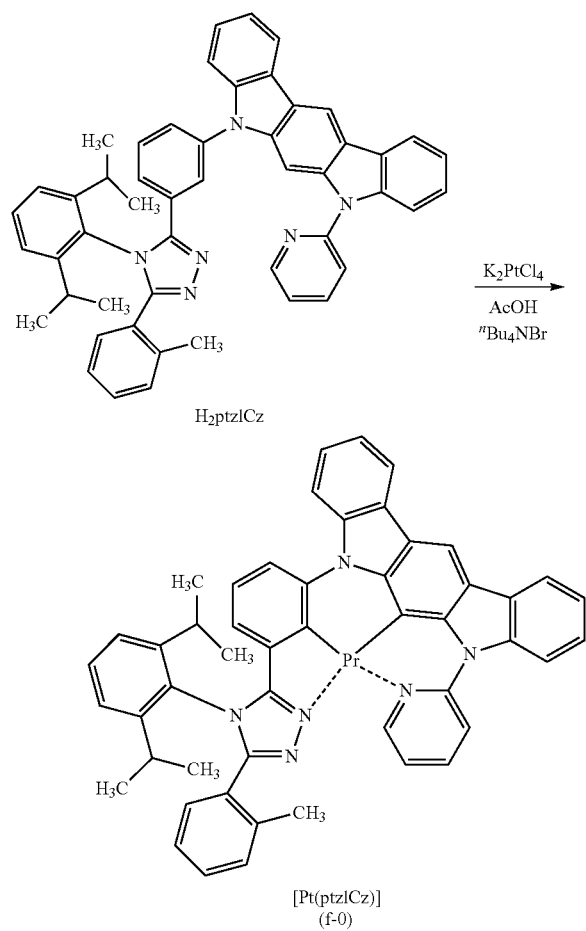

Figure 15:
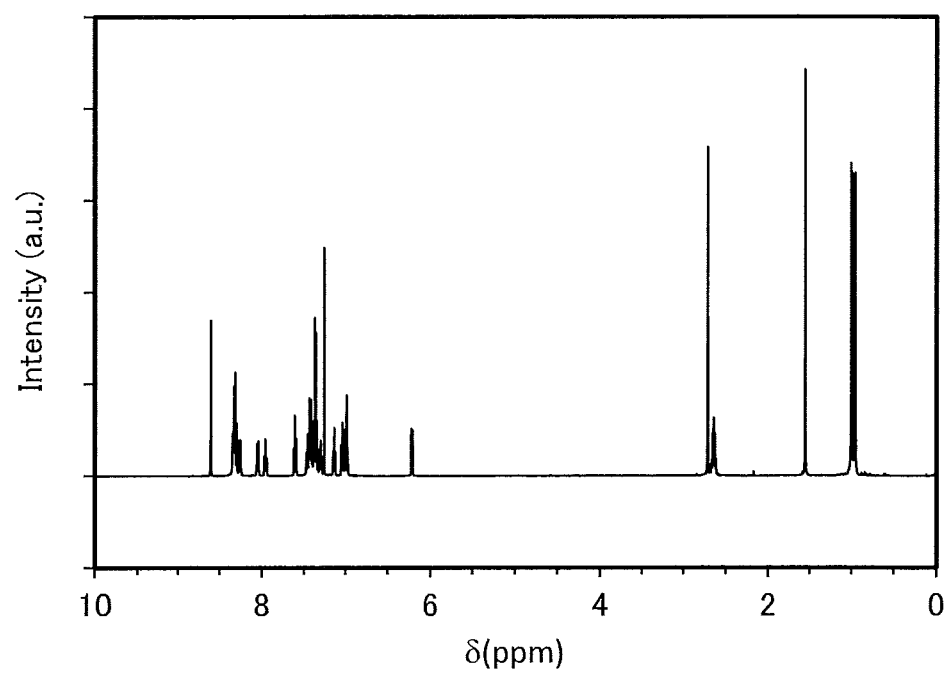
FIG. 15 is a $^1$H-NMR chart of an organometallic complex represented by the structural formula (100).

Measurements were performed on the protons ($^1$H) of the yellow solid that was obtained in Step 6 by a nuclear magnetic resonance (NMR) method. The obtained values are shown below. FIG. 15 shows the $^1$H-NMR chart. These results revealed that [Pt(ptzICz)], the organometallic complex according to the present invention which is represented by the above structural formula (100), was obtained in Synthesis Example 1.

$^1$H-NMR. δ (CDCl$_3$): 0.98 (dd, 12H), 2.60-2.68 (m, 2H), 2.71 (s, 3H), 6.22 (d, 1H), 6.97-7.05 (m, 3H), 7.14 (t, 1H), 7.28-7.47 (m, 8H), 7.61 (t, 1H), 7.95 (t, 1H), 8.04-8.06 (m, 1H), 8.24-8.35 (m, 5H), 8.60 (s, 1H), 10.78 (d, 1H).

Figure 16A:
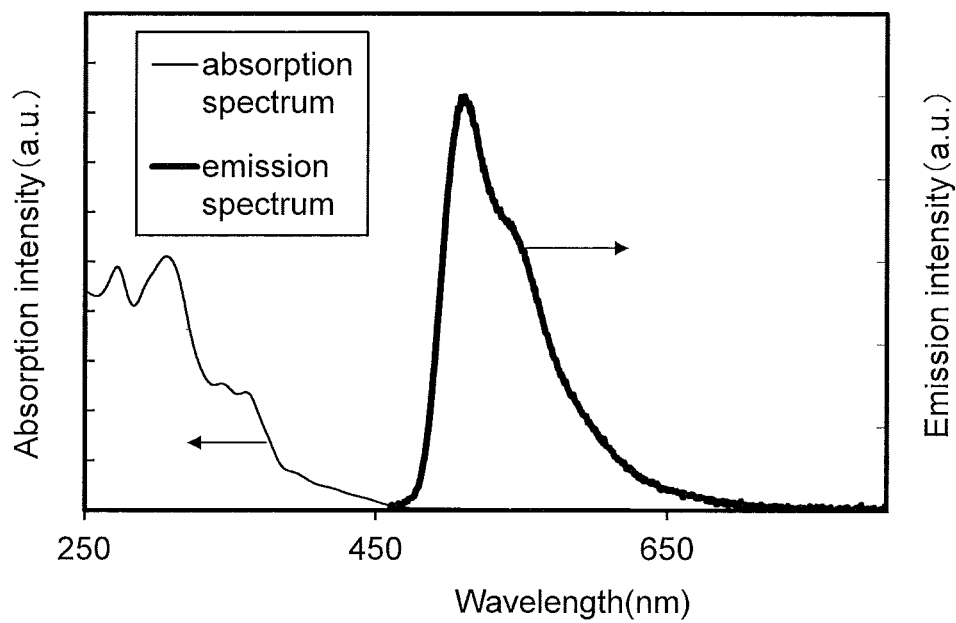
FIGS. 16A and 16B are graphs showing the ultraviolet-visible absorption spectrum and the emission spectrum of the organometallic complex represented by the structural formula (100).
Figure 16B:
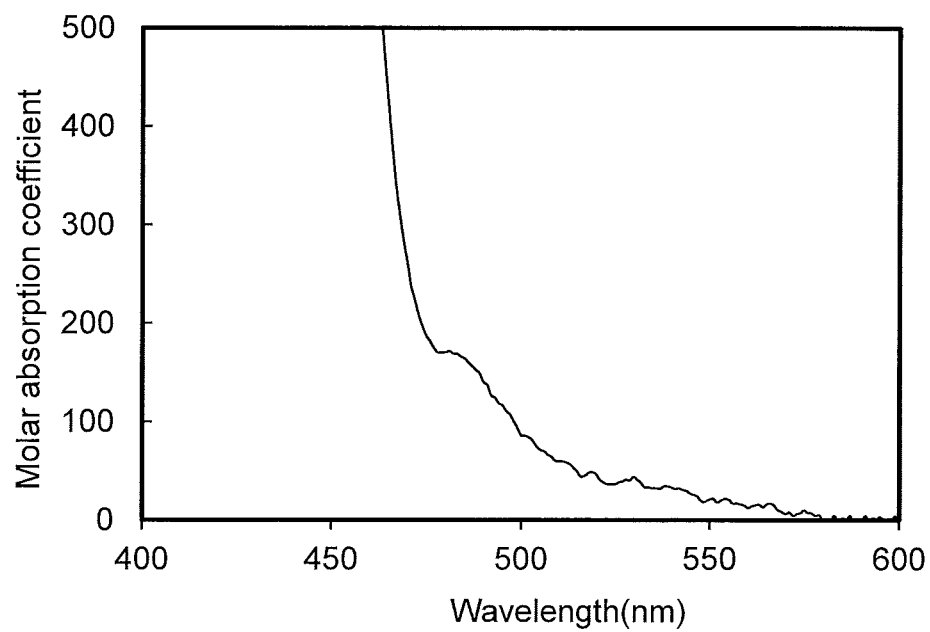

Next, an ultraviolet-visible absorption spectrum (hereinafter, simply referred to as absorption spectrum) and an emission spectrum of a dichloromethane solution of [Pt(ptzICz)] were measured. The absorption spectrum was measured with an ultraviolet-visible light spectrophotometer (V550 type, produced by JASCO Corporation) at room temperature in the state where the dichloromethane solution (0.0010 mmol/L) was in a quartz cell. In addition, the measurement of the emission spectrum was performed at room temperature in such a manner that an absolute PL quantum yield measurement system (C11347-01 manufactured by Hamamatsu Photonics K. K.) was used and the deoxidized dichloromethane solution (0.0010 mmol/L) was sealed in a quartz cell under a nitrogen atmosphere in a glove box (LABstar M13 (1250/780) manufactured by Bright Co., Ltd.). FIG. 16A shows measurement results of the absorption spectrum and the emission spectrum. The horizontal axis represents wavelength and the vertical axes represent absorption intensity and emission intensity. In the absorption spectrum shown in FIG. 16A, absorption considered to be transition from the singlet ground state to the triplet excited state is shown in FIG. 16B. The horizontal axis represents wavelength and the vertical axis represents absorption intensity (molar absorption coefficient L/(mol·cm)). Note that the absorption spectrum in FIGS. 16A and 16B, is a result obtained by subtraction of a measured absorption spectrum of only dichloromethane that was put in a quartz cell from the measured absorption spectrum of the dichloromethane solution (0.0010 mmol/L) in a quartz cell. The quantum yield was 0.92.

As shown in FIG. 16A, the platinum complex [Pt(ptzICz)] has an emission peak at 510 nm, and green light emission from the dichloromethane was observed. Furthermore, as shown in FIG. 16B, in the platinum complex [Pt(ptzICz)], strong absorption based on transition from the singlet ground state to the triplet excited state was observed at 470 nm to 550 nm.

Next, [Pt(ptzICz)] obtained in this example was subjected to a MS analysis by liquid chromatography mass spectrometry (LC/MS).

In the LC/MS, liquid chromatography (LC) separation was carried out with ACQUITY UPLC (registered trademark) which was produced by Waters Corporation and mass spectrometry (MS) was carried out with Xevo G2 Tof MS (produced by Waters Corporation). ACQUITY UPLC BEH C8 (2.1×100 mm, 1.7 µm) was used as a column for the LC separation, and the column temperature was 40° C. Acetonitrile was used for Mobile Phase A and a 0.1% formic acid aqueous solution was used for Mobile Phase B. Furthermore, a sample was prepared in such a manner that [Pt(ptzICz)] was dissolved in chloroform at a given concentration and the mixture was diluted with acetonitrile. The injection amount was 5.0 µL.

In the LC separation, a gradient method in which the composition of mobile phases is changed was employed. The ratio of Mobile Phase A to Mobile Phase B was 75:25 for 0 to 1 minute after the start of the measurement, and then the composition was changed such that the ratio of Mobile Phase A to Mobile Phase B after 10 minutes from the start of the measurement was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 919.30 that underwent the ionization under the above-described conditions was collided with an argon gas in a collision cell to dissociate into product ions. Energy (collision energy) for the collision with argon was 70 eV. A mass range for the measurement was m/z=100-1200. The detection result of the dissociated product ions by time-of-flight (TOF) MS are shown in FIG. 17.

Figure 17:
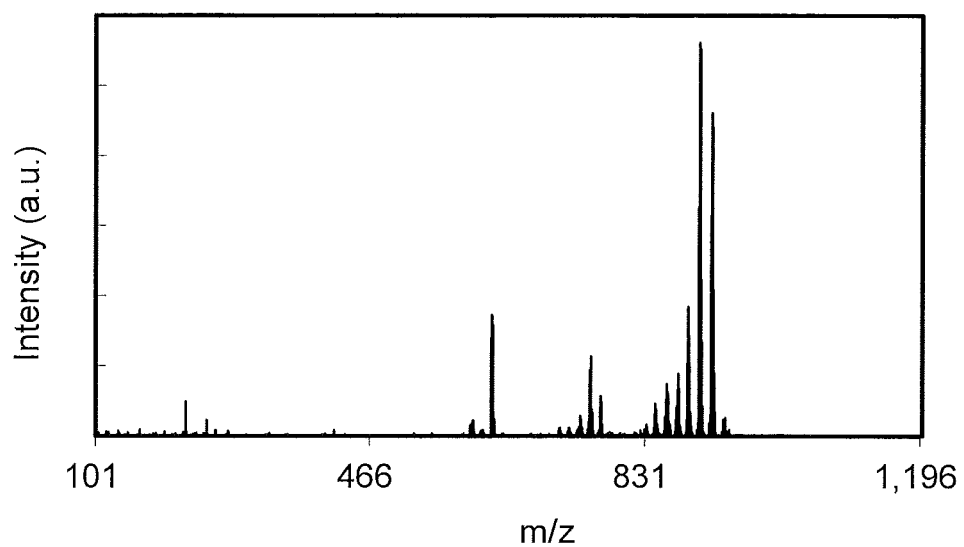
FIG. 17 shows LC/MS analysis results of the organometallic complex represented by the structural formula (100).

The results in FIG. 17 show that product ions of [Pt(ptzICz)] are detected mainly around m/z=903, m/z=888, m/z=875, m/z=859, m/z=844, m/z=771, m/z=757, m/z=627, and m/z=221. The results in FIG. 17 show characteristics derived from [Pt(ptzICz)] and can thus be regarded as important data in identification of [Pt(ptzICz)] contained in a mixture.

EXAMPLE 2

Figure 18:
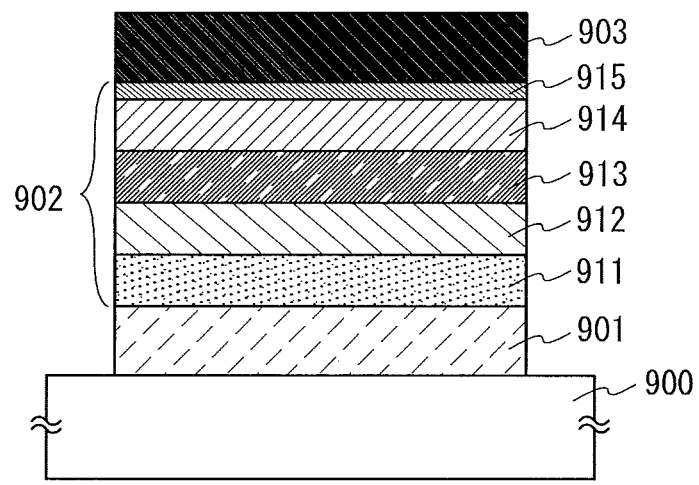
FIG. 18 illustrates a structure of a light-emitting element.

In this example, a light-emitting element 1 and a light-emitting element 2 each including [Pt(ptzICz)] (represented by the structural formula (100)) which is an organometallic complex of one embodiment of the present invention were fabricated. Note that the fabrication of the light-emitting elements is described with reference to FIG. 18. Chemical formulae of materials used in this example are shown below.

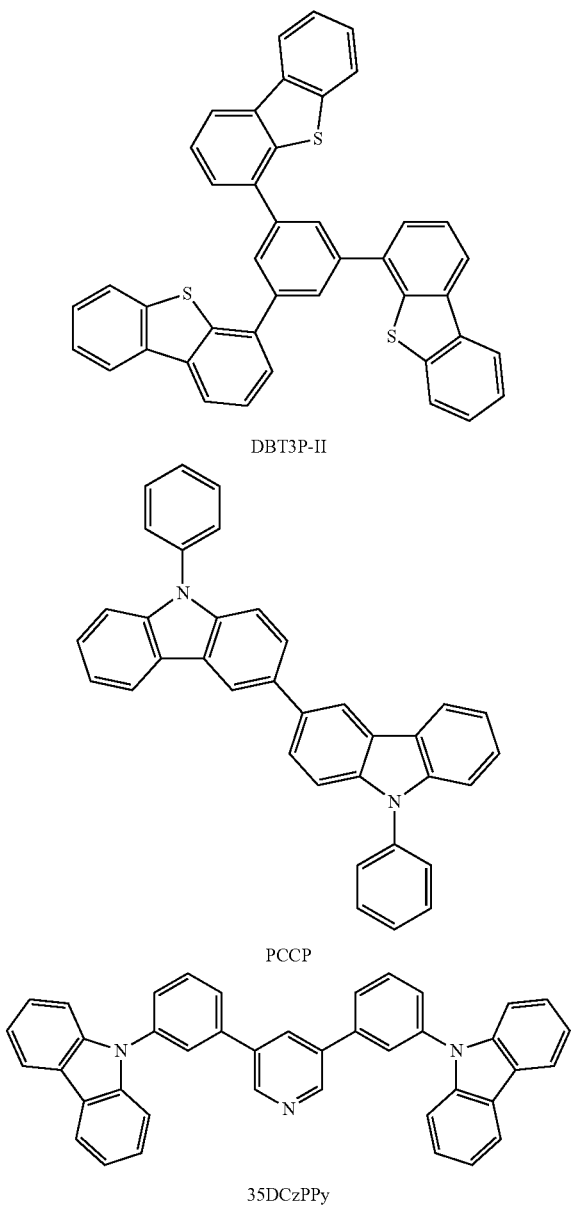

DBT3P-II

PCCP

35DCzPPy

-continued

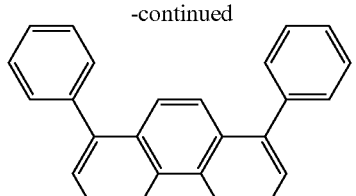

Bphen

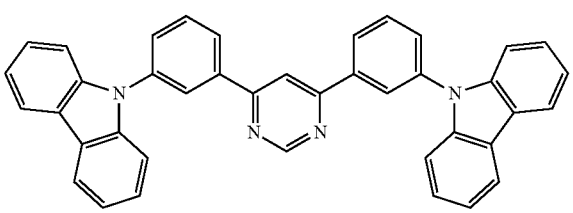

4,6mCzP2Pm

[Pt(ptz)]Cz]

<<Fabrication of Light-Emitting Element>>

First, indium tin oxide (ITO) containing silicon oxide was deposited over a glass substrate 900 by a sputtering method, whereby a first electrode 901 functioning as an anode was formed. The thickness of the first electrode 901 was 70 nm and the electrode area was 2 mm×2 mm.

Next, as pretreatment for forming the light-emitting element over the substrate 900, UV ozone treatment was performed for 370 seconds after washing of a surface of the substrate with water and baking that was performed at 200° C. for 1 hour.

After that, the substrate 900 was transferred into a vacuum evaporation apparatus where the pressure had been reduced to approximately $1\times10^{-4}$ Pa, and was subjected to vacuum baking at 170° C. for 30 minutes in a heating chamber of the vacuum evaporation apparatus. Then, the substrate 900 was cooled down for approximately 30 minutes.

Next, the substrate 900 over which the first electrode 901 was formed was fixed to a holder provided inside a vacuum evaporation apparatus so that the surface over which the first electrode was formed faced downward. In this example, a case will be described in which a hole-injection layer 911, a hole-transport layer 912, a light-emitting layer 913, an electron-transport layer 914, and an electron-injection layer 915 which are included in an EL layer 902 are sequentially formed by a vacuum evaporation method.

After reducing the pressure of the vacuum evaporation apparatus to $1\times10^{-4}$ Pa, 1,3,5-tri(dibenzothiophen-4-yl)benzene (abbreviation: DBT3P-II) and molybdenum oxide were co-evaporated at a mass ratio of 4:2 (DBT3P-II: molybdenum oxide), whereby the hole-injection layer 911 was formed over the first electrode 901. The thickness was set to 60 nm. Note that a co-evaporation method is an evaporation method in which a plurality of different substances is concurrently vaporized from respective different evaporation sources.

Then, 9-phenyl-9H-3-(9-phenyl-9H-carbazol-3-yl)carbazole (abbreviation: PCCP) was deposited by evaporation to a thickness of 20 nm, whereby the hole-transport layer 912 was formed.

Next, the light-emitting layer 913 was formed on the hole-transport layer 912.

In the case of the light-emitting element 1, 9-phenyl-9H-3-(9-phenyl-9H-carbazol-3-yl)carbazole (abbreviation: PCCP), 3,5-bis[3-(9H-carbazol-9-yl)phenyl]pyridine (abbreviation: 35DCzPPy), and [Pt(ptzICz)] are co-evaporated to a thickness of 20 nm with a mass ratio of PCCP to 35DczPPy and [Pt(ptzICz)] being 0.5:0.5:0.05, and then are co-evaporated to a thickness of 20 nm with a mass ratio of PCCP to 35DczPPy and [Pt(ptzICz)] being 0.8:0.2:0.05, whereby the light-emitting layer 913 having a stacked-layer structure was formed with a thickness of 40 nm.

In the case of the light-emitting element 2, PCCP, 9,9'-(pyrimidine-4,6-diyldi-3,1-phenylene)bis(9H-carbazole) (abbreviation: 4,6mCzP2Pm), and [Pt(ptzICz)] are co-evaporated to a thickness of 20 nm with a mass ratio of PCCP to 4,6mCzP2Pm and [Pt(ptzICz)] being 0.5:0.5:0.05, and then are co-evaporated to a thickness of 20 nm with a mass ratio of PCCP to 4,6mCzP2Pm and [Pt(ptzICz)] being 0.8:0.2:0.05, whereby the light-emitting layer 913 having a stacked-layer structure was formed with a thickness of 40 nm.

Next, in the case of the light-emitting element 1, the electron-transport layer 914 was formed over the light-emitting layer 913 in such a manner that 35DczPPy was evaporated to a thickness of 15 nm, and then Bphen was evaporated to a thickness of 15 nm. In the case of the light-emitting element 2, the electron-transport layer 914 was formed in such a manner that 4,6mCzP2Pm was evaporated to a thickness of 20 nm, and then Bphen was evaporated to a thickness of 10 nm.

Furthermore, lithium fluoride was evaporated to a thickness of 1 nm over the electron-transport layer 914, whereby the electron-injection layer 915 was formed.

Finally, aluminum was deposited to a thickness of 200 nm over the electron-injection layer 915, whereby a second electrode 903 functioning as a cathode was formed. Thus, the light-emitting elements 1 and 2 were fabricated. It is to be noted that an evaporation method using resistive heating was employed for all the evaporation steps.

Element structures of the light-emitting elements 1 and 2 obtained in the above manner are shown in Table 1.

TABLE 1

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITO (70 nm) | DBT3P-II:MoOx (4:2 60 nm) | PCCP (20 nm) | * | 35DCzPPy (15 nm) | Bphen (15 nm) | LiF (1 nm) | Al (200 nm) |
| Light-emitting Element 2 | ITO (70 nm) | DBT3P-II:MoOx (4:2 60 nm) | PCCP (20 nm) | ** | 4,6mCzP2Pm (20 nm) | Bphen (10 nm) | LiF (1 nm) | Al (200 nm) |

* PCCP:35DCzPPy:[Pt(ptzICz)]\PCCP:35DCzPPy:[Pt(ptzICz)] (0.5:0.5:0.05 20 nm\0.8:0.2:0.05 20 nm)

** PCCP:4,6mCzP2Pm:[Pt(ptzICz)]\PCCP:4,6mCzP2Pm:[Pt(ptzICz)](0.5:0.5:0.05 20 nm\0.8:0.2:0.05 20 nm)

Furthermore, the fabricated light-emitting elements were sealed in a glove box under a nitrogen atmosphere so as not to be exposed to the air (specifically, a sealant was applied to surround the element, and at the time of sealing, first, UV treatment was performed and then heat treatment was performed at 80° C. for 1 hour).

<<Operation Characteristics of Light-Emitting Element>>

Operation characteristics of the fabricated light-emitting elements 1 and 2 were measured. It is to be noted that the measurements were performed at room temperature (in an atmosphere kept at 25° C.).

Figure 19:
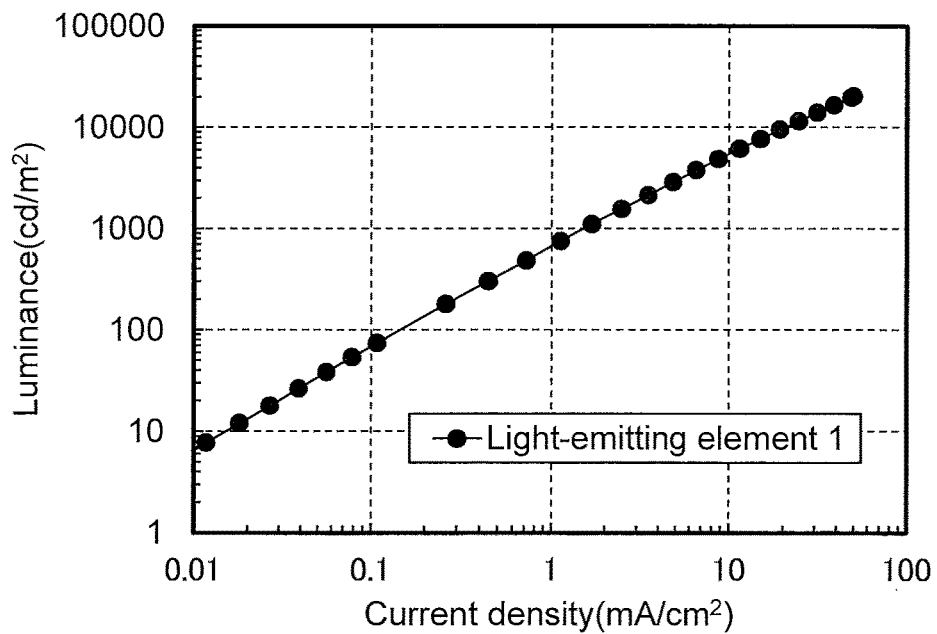
FIG. 19 shows current density-luminance characteristics of Light-emitting Element 1.
Figure 20:
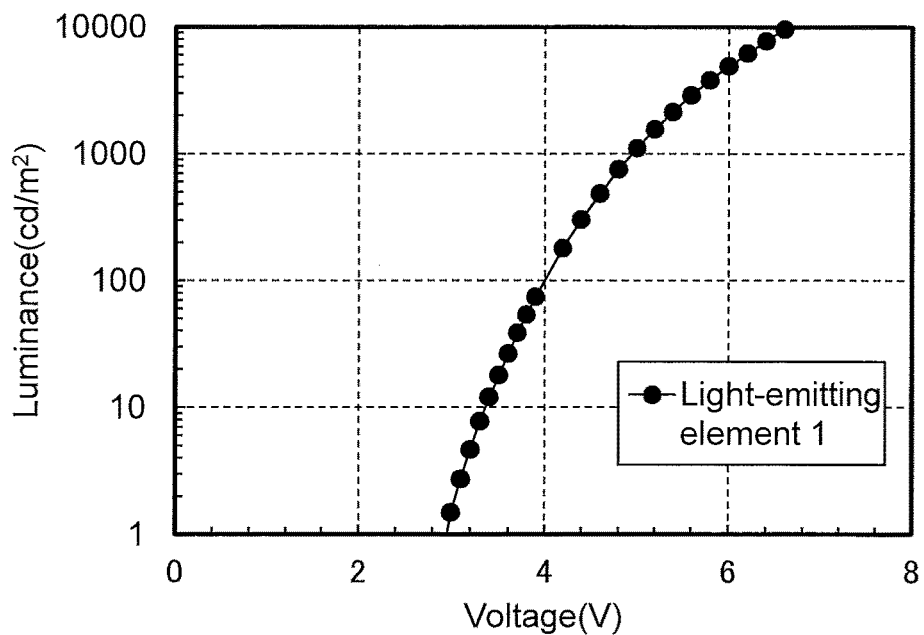
FIG. 20 shows voltage-luminance characteristics of Light-emitting Element 1.
Figure 21:
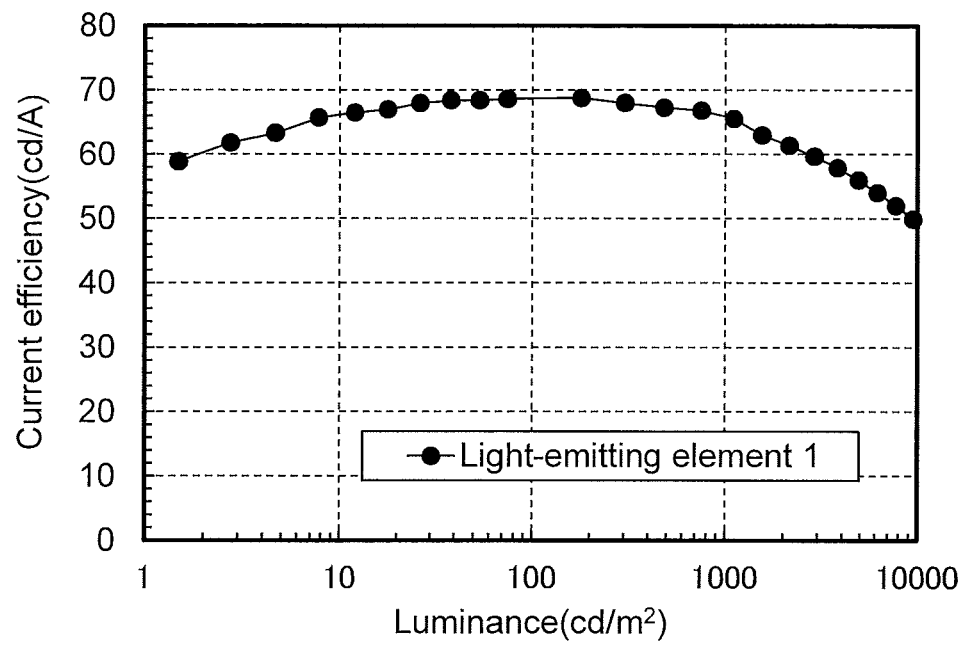
FIG. 21 shows luminance-current efficiency characteristics of Light-emitting Element 1.
Figure 22:
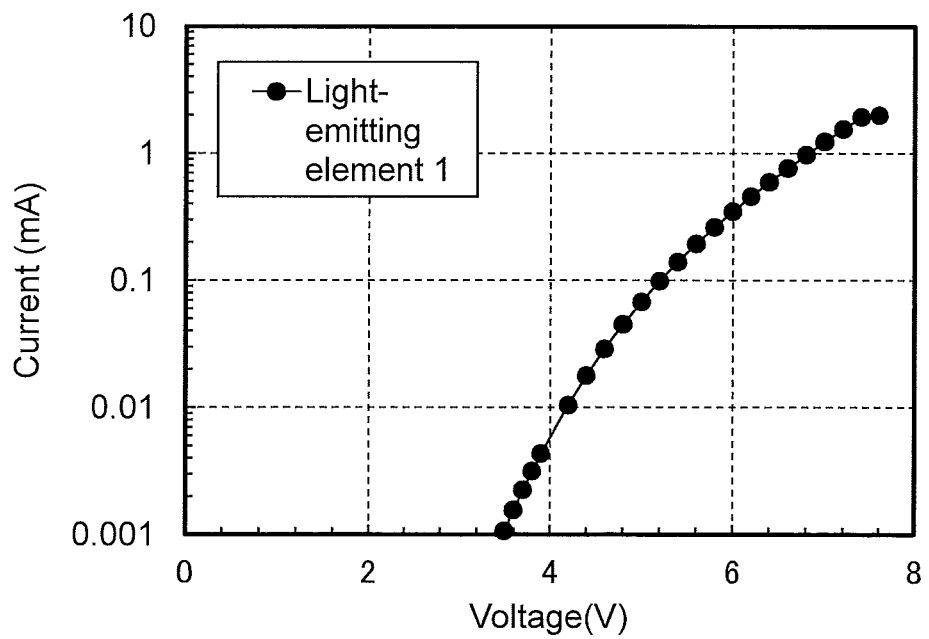
FIG. 22 shows voltage-current characteristics of Light-emitting Element 1.
Figure 23:
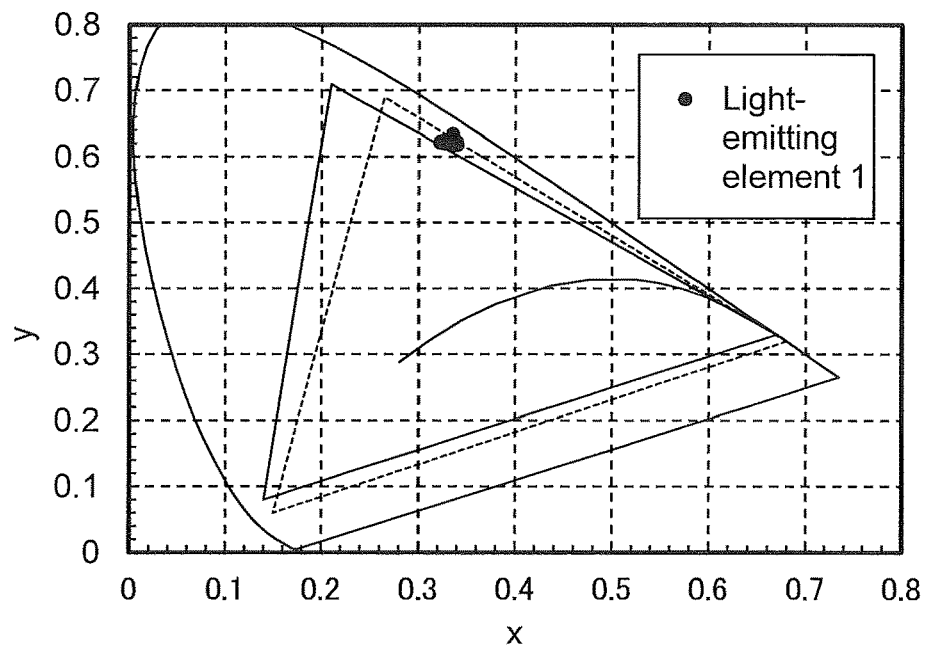
FIG. 23 shows chromaticity coordinates of Light-emitting Element 1.
Figure 25:
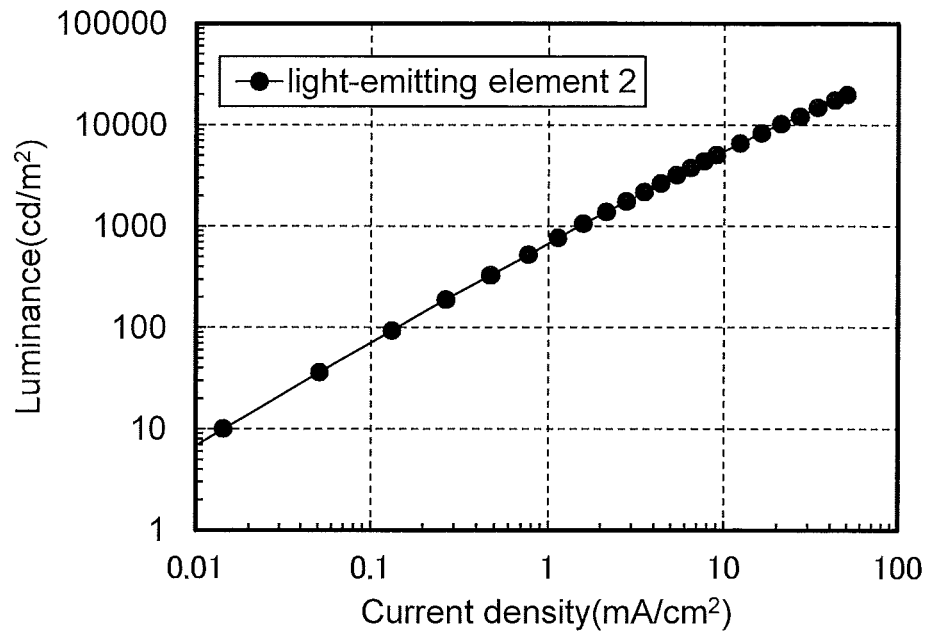
FIG. 25 shows current density-luminance characteristics of Light-emitting Element 2.
Figure 26:
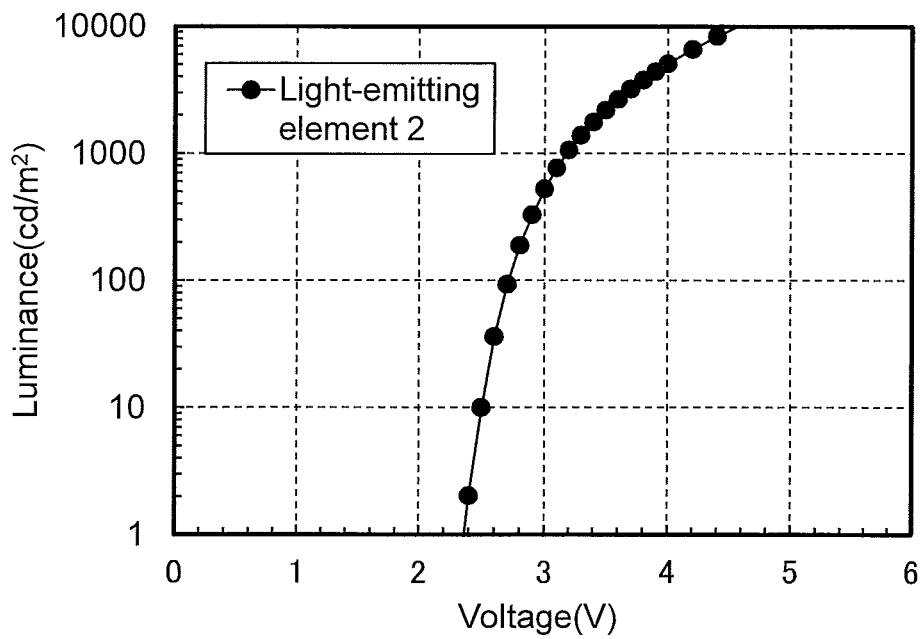
FIG. 26 shows voltage-luminance characteristics of Light-emitting Element 2.
Figure 27:
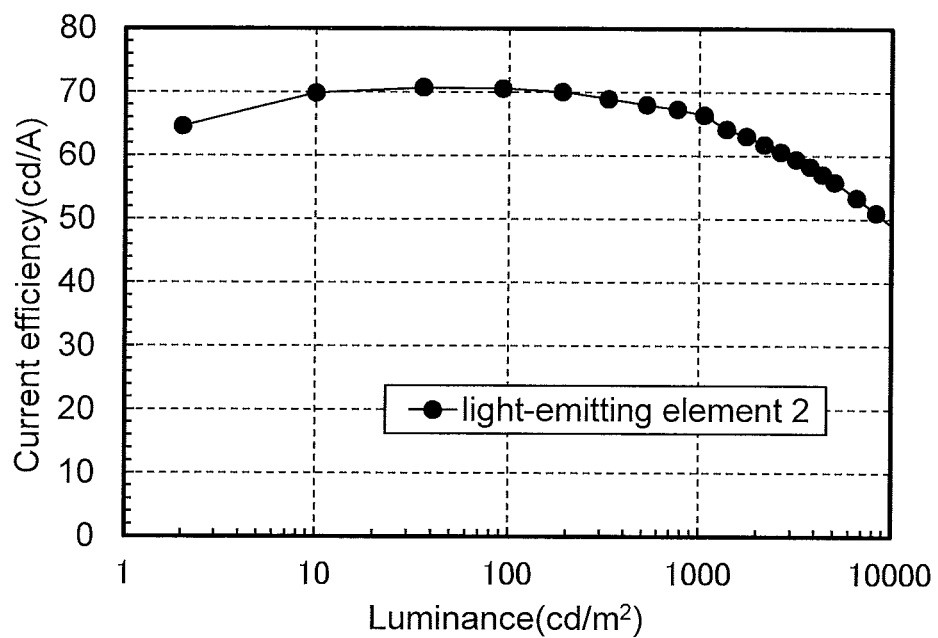
FIG. 27 shows luminance-current efficiency characteristics of Light-emitting Element 2.
Figure 28:
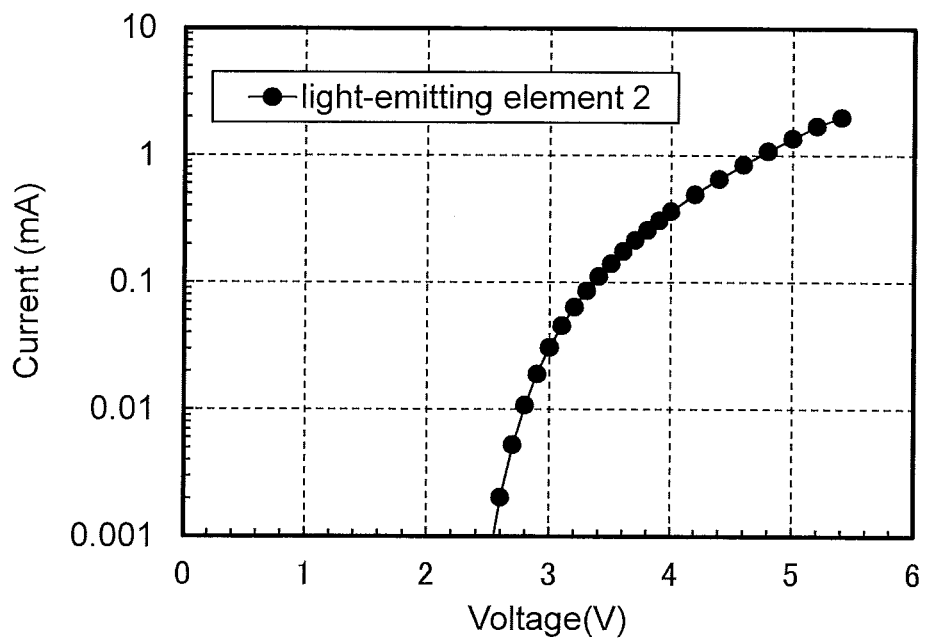
FIG. 28 shows voltage-current characteristics of Light-emitting Element 2.
Figure 29:
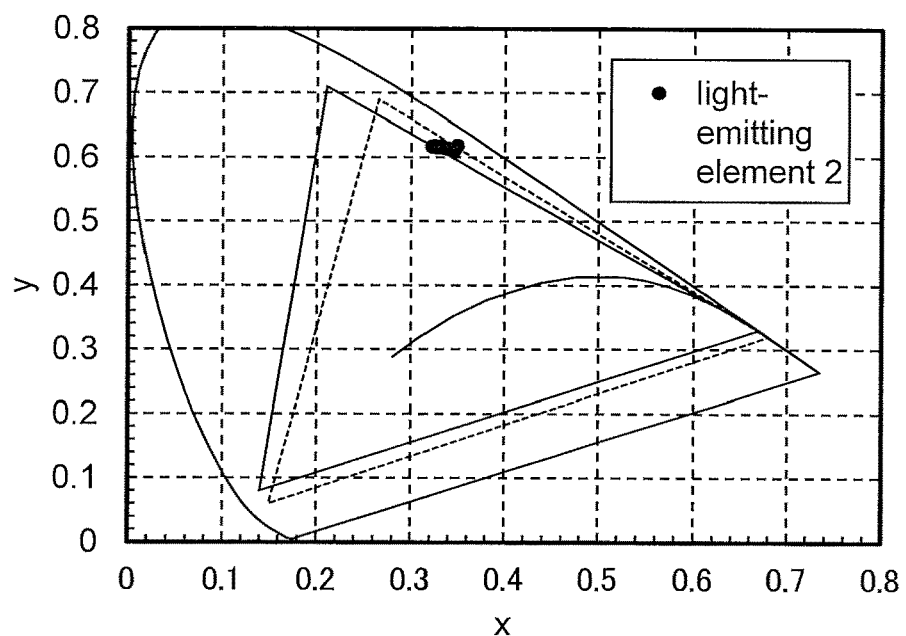
FIG. 29 shows chromaticity coordinates of Light-emitting Element 2.

FIG. 19 shows current density-luminance characteristics of the light-emitting element 1, FIG. 20 shows voltage-luminance characteristics of the light-emitting element 1, FIG. 21 shows luminance-current efficiency characteristics of the light-emitting element 1, FIG. 22 shows voltage-current characteristics of the light-emitting element 1, and FIG. 23 shows chromaticity coordinates of the light-emitting element 1. FIG. 25 shows current density-luminance characteristics of the light-emitting element 2, FIG. 26 shows voltage-luminance characteristics of the light-emitting element 2, FIG. 27 shows luminance-current efficiency characteristics of the light-emitting element 2, FIG. 28 shows voltage-current characteristics of the light-emitting element 2, and FIG. 29 shows chromaticity coordinates of the light-emitting element 2.

Table 2 shows initial values of main characteristics of the light-emitting elements 1 and 2 at a luminance of about 1000 cd/m$^2$.

TABLE 2

|  | Voltage (V) | Current (mA) | Currnt Density (mA/cm²) | Chromaticity (x, y) | Luminance (cd/m²) | Current Efficiency (cd/A) | Power Efficiency (lm/W) | External Quantum Efficiency (%) |
|---|---|---|---|---|---|---|---|---|
| Light-emitting Element 1 | 5.0 | 0.068 | 1.7 | (0.33, 0.62) | 1100 | 66 | 41 | 18 |
| Light-emitting Element 2 | 3.2 | 0.064 | 1.6 | (0.33, 0.62) | 1100 | 66 | 65 | 19 |

Figure 24:
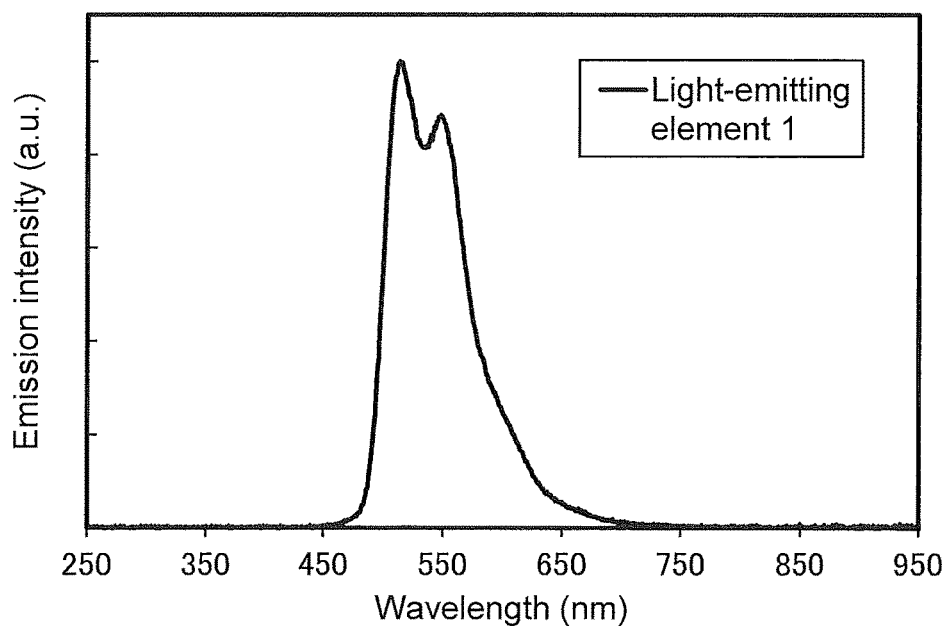
FIG. 24 shows an emission spectrum of Light-emitting Element 1.
Figure 30:
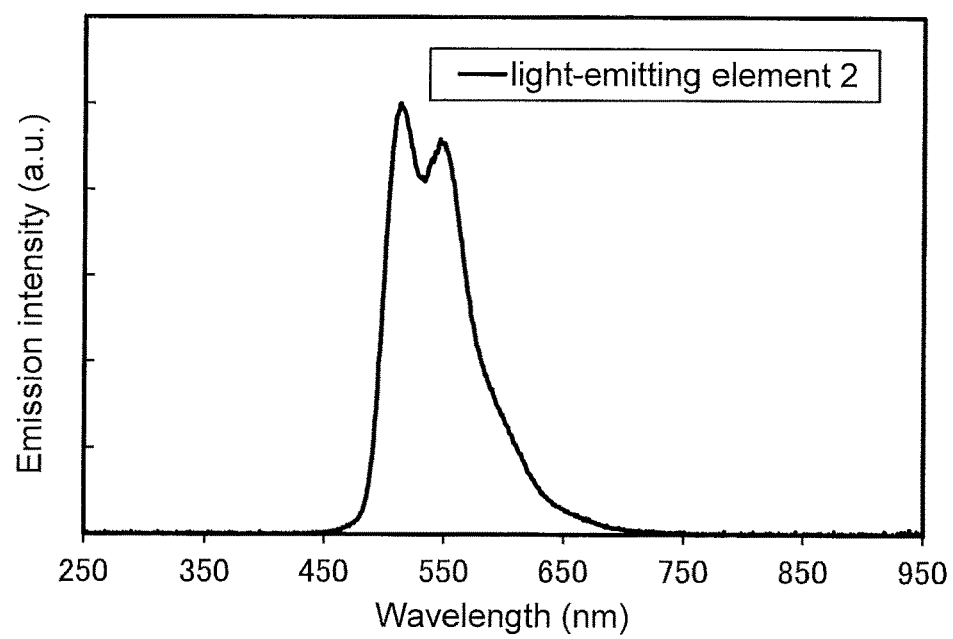
FIG. 30 shows an emission spectrum of Light-emitting Element 2.

FIG. 24 shows an emission spectrum when a current at a current density of 1.7 mA/cm² was supplied to the light-emitting element 1, and FIG. 30 shows an emission spectrum when a current at a current density of 1.6 mA/cm² was supplied to the light-emitting element 2. The emission spectrum of the light-emitting element 1 has peaks at around 514 nm and around 549 nm in FIG. 24, and the emission spectrum of the light-emitting element 2 has peaks at around 513 nm and around 546 nm in FIG. 30. Accordingly, it is suggested that the peaks are derived from green light emission of the organometallic complex, [Pt(ptzlCz)], used in the EL layer of each of the light-emitting elements 1 and 2.

This application is based on Japanese Patent Application serial no. 2015-102410 filed with Japan Patent Office on May 20, 2015, the entire contents of which are hereby incorporated by reference.

What is claimed is:

1. A light-emitting element comprising:
an EL layer between a pair of electrodes,
wherein the EL layer comprises a light-emitting layer, and
wherein the light-emitting layer comprises an organometallic complex represented by a formula (G1-1),

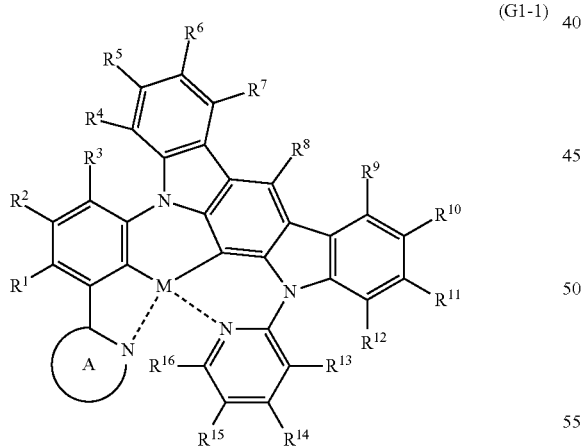

(G1-1)

wherein M represents Pt or Pd, and each of $R^1$ to $R^{16}$ independently represents any one of hydrogen, an alkyl group having 1 to 6 carbon atoms, and a substituted or unsubstituted aryl group having 6 to 13 carbon atoms,
wherein a ring A represents a triazole ring, and
wherein the light-emitting element emits green light.

2. The light-emitting element according to claim 1, wherein when the ring A is represented by a formula (α), the foimula (α) is any one of a formula (α-1), a formula (α-2), a formula (α-3), and a formula (α-4) below,

(α)

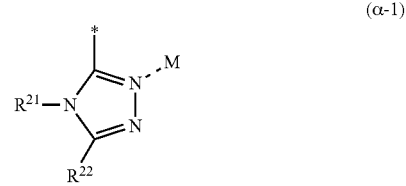

(α-1)

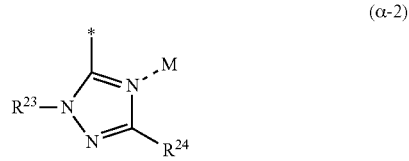

(α-2)

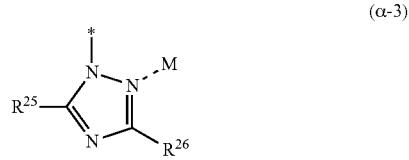

(α-3)

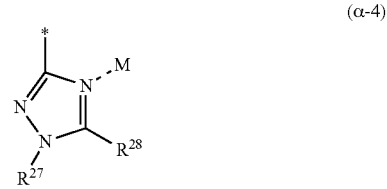

(α-4)

wherein each of $R^{21}$ to $R^{28}$ independently represents any one of hydrogen, an alkyl group having 1 to 6 carbon atoms, and a substituted or unsubstituted aryl group having 6 to 13 carbon atoms.

3. The light-emitting element according to claim 1, wherein the organometallic complex is represented by a formula (100) below.

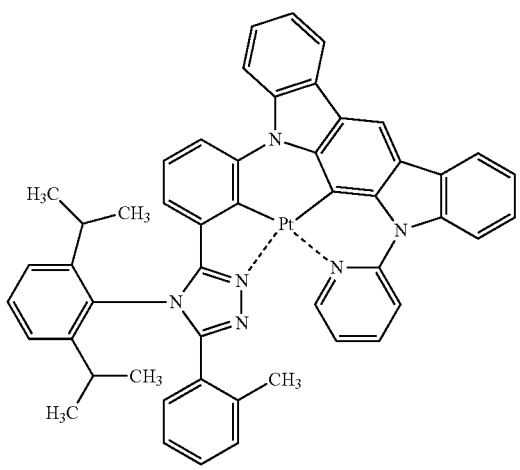

(100)

4. The light-emitting element according to claim 1,
wherein the light-emitting layer comprises a guest material and a host material, and
wherein the guest material is the organometallic complex represented by the formula (G1-1).

5. A light-emitting device comprising:
the light-emitting element according to claim 1; and
any one of a transistor and a substrate.

6. An electronic device comprising:
the light-emitting device according to claim 5; and
any one of a microphone, a camera, an operation button, an external connection portion, and a speaker.

7. An electronic device comprising:
the light-emitting device according to claim 5; and
a housing or a touch sensor.

8. A lighting device comprising:
the light-emitting device according to claim 5; and
any one of a housing, a cover, and a support.

9. The light-emitting element according to claim 4,
wherein the host material has higher triplet excitation energy than the guest material.

10. The light-emitting element according to claim 4,
wherein the host material comprises a n-electron deficient heteroaromatic compound.

11. The light-emitting element according to claim 4,
wherein the host material comprises a n-electron rich heteroaromatic compound.

12. The light-emitting element according to claim 4,
wherein the host material comprises an aromatic amine compound.

* * * * *